US012595281B2

(12) United States Patent
Medintz et al.

(10) Patent No.: US 12,595,281 B2
(45) Date of Patent: Apr. 7, 2026

(54) INDODICARBOCYANINE PHOSPHORAMIDITES WITH BATHOCHROMICALLY SHIFTED ABSORPTION AND EMISSION, AND TUNABLE HYDROPHOBICITY

(71) Applicant: The Government of the United States of America, as represented by the Secretary of the Navy, Arlington, VA (US)

(72) Inventors: Igor L. Medintz, Washington, DC (US); Joseph Melinger, Washington, DC (US); William B. Knowlton, Boise, ID (US); Bernard Yurke, Boise, ID (US); Kimihiro Susumu, Washington, DC (US); Sang Ho Lee, Washington, DC (US); Adam Meares, Fairfax, VA (US); Divita Mathur, Fairfax, VA (US); Olga A. Mass, Boise, ID (US); Jeunghoon Lee, Boise, ID (US); Ryan D. Pensack, Boise, ID (US)

(73) Assignee: The Government of the United States of America, as represented by the Secretary of the Navy, Arlington, VA (US)

(*) Notice: Subject to any disclaimer, the term of this patent is extended or adjusted under 35 U.S.C. 154(b) by 615 days.

(21) Appl. No.: 18/160,925

(22) Filed: Jan. 27, 2023

(65) Prior Publication Data

US 2023/0250126 A1 Aug. 10, 2023

Related U.S. Application Data

(60) Provisional application No. 63/307,328, filed on Feb. 7, 2022.

(51) Int. Cl.
*C07H 21/00* (2006.01)

(52) U.S. Cl.
CPC .................................... *C07H 21/00* (2013.01)

(58) Field of Classification Search
None
See application file for complete search history.

(56) References Cited

U.S. PATENT DOCUMENTS 5,556,959 A 9/1996 Brush et al.
5,808,044 A 9/1998 Brush et al.

OTHER PUBLICATIONS

Mujumdar, R. B.; Ernst, L. A.; Mujumdar, S. R.; Lewis, C. J.; Waggoner, A. S. Cyanine Dye Labeling Reagents—Sulfoindocyanine Succinimidyl Esters. Bioconjugate Chemistry 1993, 4 (2), 105-111. DOI: 10.1021/bc00020a001.

Gerowska, M.; Hall, L.; Richardson, J.; Shelbourne, M.; Brown, T. Efficient reverse click labeling of azide oligonucleotides with multiple alkynyl Cy-Dyes applied to the synthesis of HyBeacon probes for genetic analysis. Tetrahedron 2012, 68 (3), 857-864. DOI: 10.1016/j.tet.2011.11.041.

Holzhauser, C.; Berndl, S.; Menacher, F.; Breunig, M.; Gopferich, A.; Wagenknecht, H. A. Synthesis and Optical Properties of Cyanine Dyes as Fluorescent DNA Base Substitutions for Live Cell Imaging. European Journal of Organic Chemistry 2010, (7), 1239-1248. DOI: 10.1002/ejoc.200901423.

Buckhout-White, S.; Brown, C. W.; Hastman, D. A.; Ancona, M. G.; Melinger, J. S.; Goldman, E. R.; Medintz, I. L. Expanding molecular logic capabilities in DNA-scaffolded multiFRET triads. Rsc Advances 2016, 6 (100), 97587-97598. DOI: 10.1039/c6ra23079b.

Mathur, D.; Samanta, A.; Ancona, M. G.; Díaz, S. A.; Kim, Y. C.; Melinger, J. S.; Goldman, E. R.; Sadowski, J. P.; Ong, L. L.; Yin, P.; et al. Understanding Forster Resonance Energy Transfer in the Sheet Regime with DNA Brick-Based Dye Networks. ACS Nano 2021, 15, 16452-16468.

Cannon, B. L.; Kellis, D. L.; Patten, L. K.; Davis, P. H.; Lee, J.; Graugnard, E.; Yurke, B.; Knowlton, W. B. Coherent Exciton Delocalization in a Two-State DNA-Templated Dye Aggregate System. Journal of Physical Chemistry A 2017, 121 (37), 6905-6916. DOI: 10.1021/acs.jpca.7b04344.

Cunningham, P. D.; Khachatrian, A.; Buckhout-White, S.; Deschamps, J. R.; Goldman, E. R.; Medintz, I. L.; Melinger, J. S. Resonance energy transfer in DNA duplexes labeled with localized dyes. Journal of Physical Chemistry B 2014, 118 (50), 14555-14565. DOI: Doi 10.1021/Jp5065006.

Mathur, D.; Kim, Y. C.; Diaz, S. A.; Cunningham, P. D.; Rolczynski, B. S.; Ancona, M. G.; Medintz, I. L.; Melinger, J. S. Can a DNA Origami Structure Constrain the Position and Orientation of an Attached Dye Molecule? J. Phys. Chem. C 2020, 125, 1509-1522.

Fothergill, J. W.; Hernandez, A. C.; Knowlton, W. B.; Yurke, B.; Li, L., Ab Initio Studies of Exciton Interactions of Cy5 Dyes. Journal of Physical Chemistry A 2018, 122 (46), 8989-8997.

(Continued)

*Primary Examiner* — Patrick T Lewis
(74) *Attorney, Agent, or Firm* — US Naval Research Laboratory; Fariborz Moazzam

(57) ABSTRACT

New phosphoramidite Cy5 derivatives can be used in automated DNA synthesis, allowing the labeling of DNA sequences with a wider array of chromophores than are presently commercially available. In addition to varying dye hydrophobicity/hydrophilicity, the 5,5'-substituents (including hexyloxy, triethyleneglycol monomethyl ether, tert-butyl, and chloro groups) can modulate electron donating/withdrawing character while also tuning resulting absorption and emission properties. Modification of the Cy5 periphery enables the tuning of photophysical properties, such as absorption and emission maxima, fluorescence quantum yield, and fluorescence lifetime.

15 Claims, 8 Drawing Sheets

Specification includes a Sequence Listing.

(56) References Cited

OTHER PUBLICATIONS

Biaggne, A.; Knowlton, W. B.; Yurke, B.; Lee, J.; Li, L., Substituent Effects on the Solubility and Electronic Properties of the Cyanine Dye Cy5: Density Functional and Time-Dependent Density Functional Theory Calculations. Molecules 2021, 26 (3).

Cy5-hex: R = $-O(CH_2)_5CH_3$
Cy5-Peg: R = $-O(CH_2CH_2O)_3CH_3$
Cy5-tBu: R = $-C(CH_3)_3$
Cy5-Cl: R = -Cl MMTr =

Cy5-hex: 25%
Cy5-Peg: 32%
Cy5-tBu: 32%
Cy5-Cl: 50%

5-hex
5-Peg
5-tBu
5-Cl

MMTr-Cl
CH₂Cl₂ and Et₃N,
or
pyridine

Cy5-hex
Cy5-Peg
Cy5-tBu
Cy5-Cl (i-Pr)₂EtN, CH₂Cl₂

Cy5-hex-phos
Cy5-Peg-phos
Cy5-tBu-phos
Cy5-Cl-phos

5

6

| DNA sequence | Av. yield[1] (%) | $\lambda_{max}$ abs (nm) | $\varepsilon_{260}$ ($M^{-1} \cdot cm^{-1}$) | $\varepsilon_{Cy5}$ ($M^{-1} \cdot cm^{-1}$) | $\lambda_{max}$ em (nm) | Stokes' Shift (v, $cm^{-1}$) | $\Phi_F$ | $\Delta\Phi_F$[2] (%) | $\tau_{avg}$ (ns) | $\tau_1$ (ns) / contribution | $\tau_2$ (ns) / contribution |
|---|---|---|---|---|---|---|---|---|---|---|---|
| **Cy5-hex series:** | | | | | | | | | | | |
| HJA | 10.3 | 673 | 260,900 | 216,000 | 696 | 491 | 0.08 | 0.14 | 0.59 | 0.50 / 0.87 | 1.18 / 0.13 |
| HJB | 7.5 | 670 | 272,100 | 219,800 | 696 | 558 | 0.07 | 0 | 0.64 | 0.47 / 0.65 | 0.96 / 0.35 |
| HJC | 12.0 | 674 | 248,700 | 208,100 | 696 | 469 | 0.09 | 0.29 | 0.66 | 0.54 / 0.77 | 1.10 / 0.23 |
| HJD | 8.9 | 673 | 259,100 | 200,900 | 696 | 491 | 0.07 | 0 | 0.57 | 0.47 / 0.80 | 0.96 / 0.20 |
| HJAcomp | 10.5 | 671 | 268,900 | 216,700 | 697 | 556 | 0.07 | 0 | 0.63 | 0.43 / 0.52 | 0.87 / 0.48 |
| **Cy5-Peg series:** | | | | | | | | | | | |
| HJA | 11.9 | 673 | 265,200 | 214,500 | 694 | 450 | 0.10 | 0.43 | 0.83 | 0.57 / 0.48 | 1.08 / 0.52 |
| HJB | 6.7 | 670 | 276,300 | 213,800 | 693 | 495 | 0.09 | 0.29 | 0.72 | 0.55 / 0.64 | 1.03 / 0.36 |
| HJC | 12.9 | 670 | 253,000 | 209,500 | 692 | 475 | 0.10 | 0.43 | 0.67 | 0.49 / 0.63 | 0.98 / 0.37 |
| HJD | 7.8 | 674 | 264,000 | 221,400 | 693 | 407 | 0.09 | 0.29 | 0.79 | 0.55 / 0.45 | 0.99 / 0.55 |
| HJAcomp | 4.5 | 671 | 273,400 | 219,000 | 693 | 473 | 0.09 | 0.29 | 0.64 | 0.54 / 0.83 | 1.13 / 0.17 |
| **Cy5-tBu series:** | | | | | | | | | | | |
| HJA | 16 | 659 | 261,800 | 261,100 | 679 | 447 | 0.26 | 0.24 | 1.44 | 0.69 / 0.15 | 1.57 / 0.85 |
| HJB | 13.7 | 656 | 272,700 | 250,000 | 677 | 473 | 0.20 | 0 | 1.07 | 0.77 / 0.56 | 1.46 / 0.44 |
| HJC | 24.3 | 659 | 249,500 | 249,300 | 678 | 425 | 0.26 | 0.24 | 1.41 | 0.64 / 0.18 | 1.58 / 0.82 |
| HJD | 17.2 | 657 | 260,300 | 260,000 | 676 | 428 | 0.21 | 0 | 1.13 | 0.67 / 0.39 | 1.42 / 0.61 |
| HJAcomp | 12.3 | 657 | 270,000 | 269,600 | 678 | 471 | 0.21 | 0 | 1.11 | 0.68 / 0.40 | 1.39 / 0.60 |
| **Cy5-Cl series:** | | | | | | | | | | | |
| HJA | 5.0 | 656 | 267,568 | 274,200 | 674 | 407 | 0.35 | 0.30 | 1.90 | 1.89 | - |
| HJB | 10.2 | 653 | 279,236 | 288,400 | 672 | 433 | 0.27 | 0 | 1.78 | 1.78 | - |
| HJC | 16.9 | 654 | 255,372 | 269,300 | 673 | 432 | 0.37 | 0.37 | 1.98 | 1.98 | - |
| HJD | 12.7 | 654 | 265,944 | 271,100 | 671 | 387 | 0.28 | 0 | 1.63 | 0.55 / 0.12 | 1.78 / 0.88 |
| HJAcomp | 10.8 | 654 | 275,640 | 276,000 | 673 | 432 | 0.29 | 0 | 1.47 | 0.84 / 0.28 | 1.71 / 072 |

FIG. 7

INDODICARBOCYANINE PHOSPHORAMIDITES WITH BATHOCHROMICALLY SHIFTED ABSORPTION AND EMISSION, AND TUNABLE HYDROPHOBICITY

CROSS-REFERENCE TO RELATED APPLICATIONS

This application claims the benefit of U.S. Provisional Patent Application No. 63/307,328 filed Feb. 7, 2022 which is incorporated herein by reference in its entirety.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 210908.

BACKGROUND

Cyanine dyes are a ubiquitous class of chromophore in the life sciences. They have been utilized for decades in protein and antibody labelling, flow cytometry, real-time polymerase chain reaction monitoring and so on. They are highly sought after because of their large extinction coefficients and high fluorescence quantum yields, making them exceptionally bright dyes. Depending on the biomolecule and location of conjugation, cyanine requires different reactive functional groups. For internal labelling of DNA, a dual functionalization with phosphoramidite and mono- or di-methoxytrityl protected pendant alcohol moieties is necessary. Due to the challenges with handling such functional groups, the only commercially available cyanines suitable for internal labelling of DNA are simple derivatives of Cy3, Cy3.5, Cy5 and Cy5.5 that lack property-altering peripheral substituents. For some applications this is acceptable, but for others, such as Förster Resonance Energy Transfer (FRET) systems, it is desirable to optimize the spectral overlap of dyes, a task difficult to achieve with a limited dye library. In addition to FRET based probes, there has been a recent push to develop highly advanced, designer molecules capable of excitonic delocalization. Excitonic delocalization requires proper distance and alignment of dye dipole moments, something which is attainable on carefully designed DNA scaffolds. The construction of the DNA scaffolds enable one to control many facets of the dye-dye interactions such as mutual position, distance, and number of dyes, but the propensity for dyes to interact with one another, or aggregate, is also dictated by the inherent dye properties.

A need exists for a greater range of dyes suitable for labeling nucleic acids.

BRIEF SUMMARY

In a first embodiment, a Cy5 derivative comprising a compound having the structure:

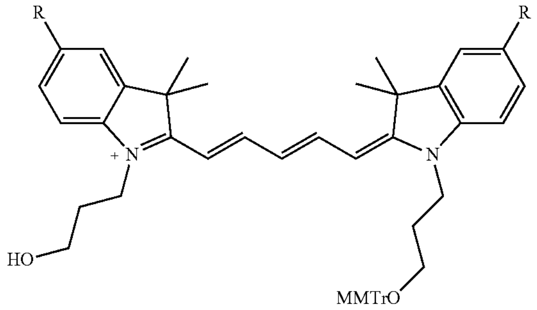

wherein MMTr is 4-monomethoxytrityl and R is selected from the group consisting of —$O(CH_2)_5CH_3$, —$O(CH_2CH_2O)_3CH_3$), —$C(CH_3)_3$, and —Cl, and wherein the Cy5 derivative includes a suitable counterion for the compound.

In a further embodiment, R is selected from the group consisting of —$CF_3$ and —CN.

Another embodiment is a nucleic acid in a state of having been synthesized to incorporate a Cy5 derivative.

Yet another embodiment is a method of synthesizing a compound of the first embodiment. In various aspects, this involves use of an iodide salt precursor and/or purification by iterative powderization.

BRIEF DESCRIPTION OF THE DRAWINGS

FIG. 1A provides the structures of the homo-substituted Cy5-hex, Cy5-Peg, Cy5-tBu, and Cy5-Cl derivative dyes synthesized as described herein. MMTr is the monomethoxytrityl protective group. These were prepared in the iodide salt form. FIG. 1B provides the structures of the Cy5 dye derivatives inserted internally into DNA oligonucleotides during phosphoramidite synthesis and attached to the DNA at both the 3' and 5' ends. The commercial Cy5 dye used for the same type of DNA labeling has the same structure but is not substituted (R=H).

FIG. 5A shows normalized absorption spectra (in terms of extinction coefficient) of the Cy5-hex (red), Cy5-Peg (blue), Cy5-tBu (pink), and Cy5-Cl (green) acquired in methanol with concentration approximated to 4-5 μM (Abs~1.0 AU). FIG. 5B provides the corresponding normalized emission spectra for the same sample series acquired in methanol with concentration approximated to 0.5 μM (Abs<0.1 AU). For emission, samples were excited at 600 nm and spectra collected from 620 to 850 nm.

FIG. 7 contains Table 3 with selected properties of the Cy5 analog-labeled DNA sequences. All values were determined in neat water. Superscript references denote the following: (1) As compared to an expected 1 μmole maximum. (2) Change compared to parent dye in MeOH. (3) $\tau_{rad}=k_{rad}^{-1}$. Extinction coefficients determined utilizing nearest-neighbor approximation for DNA absorbance at 260 nm, while also accounting for Cy5 contribution. Cy5 percent contribution (0.02-0.04) was based on ratio of absorbance at 260 nm and at Cy5 $\lambda_{max}$ for each of the parent dyes obtained in methanol. It was assumed that Cy5 percent contribution at 260 nm is constant between MeOH and $H_2O$. Fluorescence QY ($\Phi_F$) determined against 5,10,15,20-tetraphenylporphyrin standard ($\Phi_F$=0.07 in toluene).

DETAILED DESCRIPTION

Definitions

Figure 1A:
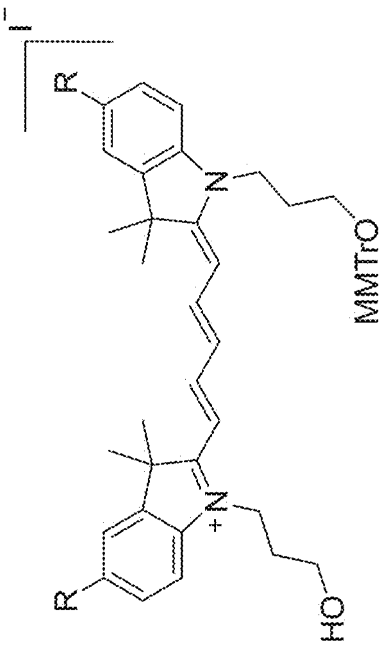
FIGS. 1A and 1B show the structure of four substituted Cy5 dye derivatives for phosphoramidite conversion and insertion in DNA.
Figure 1B:
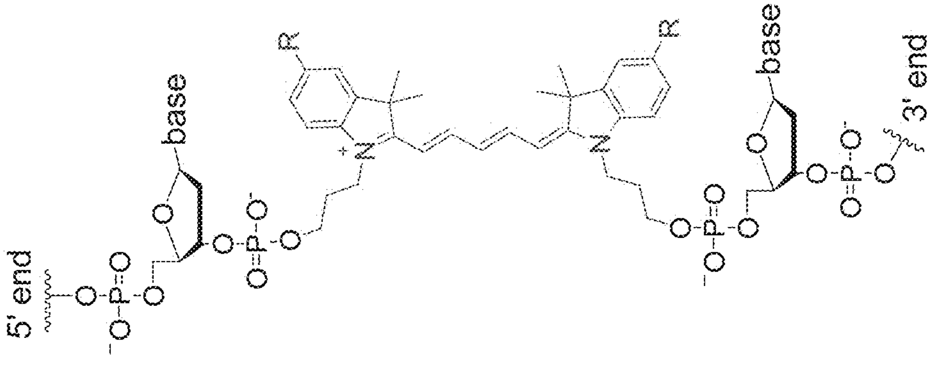

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms “a”, “an,” and “the” do not preclude plural referents, unless the content clearly dictates otherwise.

As used herein, the term “and/or” includes any and all combinations of one or more of the associated listed items.

As used herein, the term “about” when used in conjunction with a stated numerical value or range denotes somewhat more or somewhat less than the stated value or range, to within a range of ±10% of that stated.

Overview

Described herein are new Cy5-phosphoramidites useful in automated DNA synthesis, allowing the experimenter to label DNA sequences with a wider array of chromophores than presently commercially available. In addition to varying dye hydrophobicity/hydrophilicity, the 5,5'-substituents (including hexyloxy, triethyleneglycol monomethyl ether, tert-butyl, and chloro groups) were chosen so as to vary the inherent electron donating/withdrawing character while also tuning their resulting absorption and emission properties. Modification of the Cy5 periphery enables the tuning of photophysical properties, such as absorption and emission maxima, fluorescence quantum yield, and fluorescence lifetime. The ability to control hydrophilicity/hydrophobicity also offers the ability to fine tune the dye-dye interactions within complex systems designed for excitonic delocalization (sometimes called quantum coherence).

Following synthesis of the parent dyes, one of their pendant alkyl chains was functionalized with monomethoxytrityl protective groups with the remaining hydroxy terminated N-propyl linker permitting rapid, same-day phosphoramidite conversion and direct internal DNA incorporation into nascent oligonucleotides with moderate to good yields using a 1 μmole scale automated DNA synthesis. Labeled sequences were cleaved from the controlled pore glass matrix, purified by HPLC, and their photophysical properties characterized. The DNA-labeled Cy5 derivatives displayed spectroscopic properties that paralleled the parent dyes, with almost no decreases to fluorescence quantum yield.

The Cy5 derivatives, ready for phosphoramidite conversion for incorporation into nucleic acids, possess different peripheral substituents including n-hexyloxy (Cy5-hex), 2-[2-(2-methoxyethoxy)ethoxy]ethoxy (Cy5-Peg), tert-butyl (Cy5-tBu) and chloro (Cy5-Cl) groups.

Synthesis

In-depth detail of each synthetic step and the corresponding chromatographic separation, NMR results, and mass spectral analysis (where available) are provided in the Appendix. The following represents an abbreviated overview of key steps. The entire synthetic scheme was initiated from the synthesis of initial 5-substituted indole precursors via Fischer indole synthesis.

Figure 2:
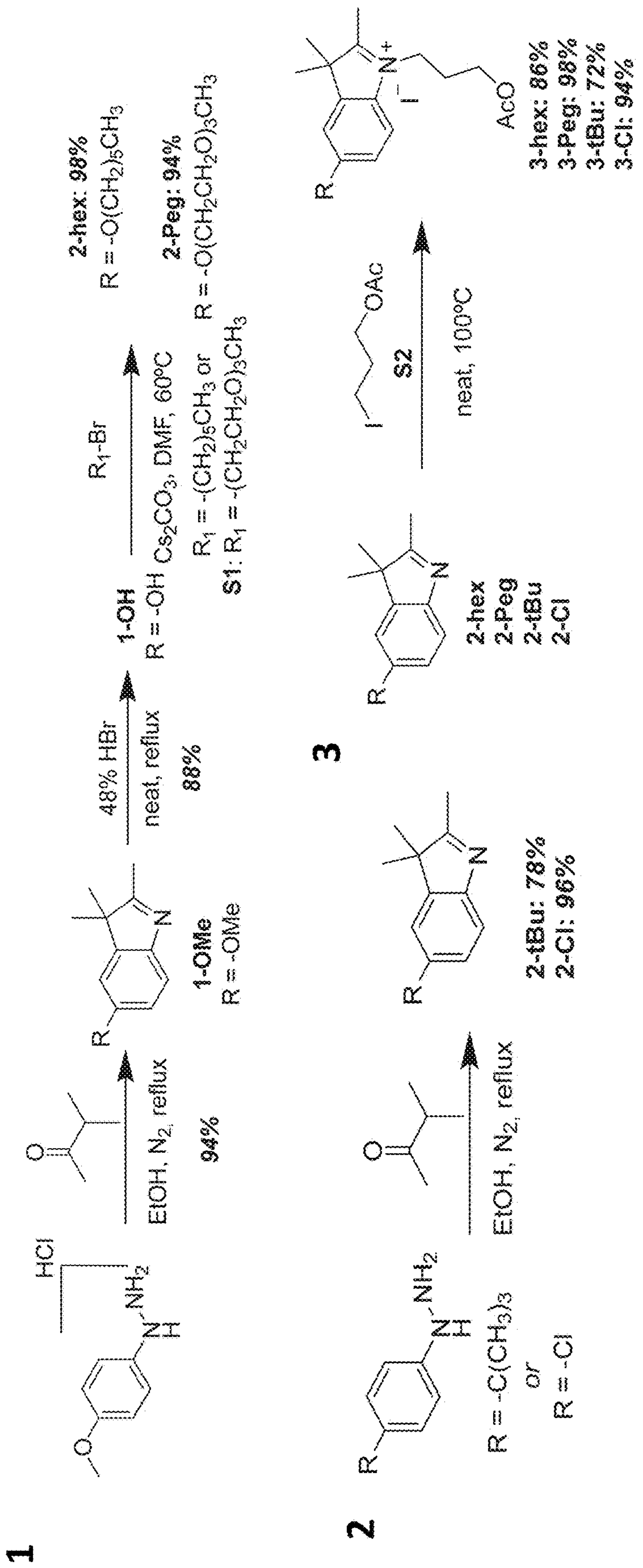
FIG. 2 illustrates synthetic Schemes 1 through 3 for obtaining the indole precursor molecules. Scheme 1 describes the synthesis of 5-alkoxy indoles. Scheme 2 describes the synthesis of 5-tert-butyl and 5-chloro indoles. Scheme 3 describes the synthesis of 5-substituted indolinium iodide salts. Yields are indicated for each step (italicized bold) following compound number. Corresponding NMR spectra and mass spectra of all products are shown in the Appendix, in order of appearance. Details for preparation of compounds S1 and S2 are found in the Appendix

For the 5-alkoxyindoles (2-hex and 2-Peg), the synthesis began by preparing 5-methoxyindole (1-OMe) from 4-methoxyphenylhydrazine hydrochloride and 3-methyl-2-butanone in refluxing ethanol (Scheme 1 in FIG. 2). The methoxy group in compound 1-OMe was then hydrolyzed in 48% aqueous hydrobromic acid, yielding the common precursor 1-OH. Next 5-hydroxyindole 1-OH, was utilized in Williamson-type ether synthesis, yielding either the 5-hexyloxy (2-hex) or 5-triethyleneglycol monomethyl ether (2-Peg) substituted indoles from bromohexane and 1-bromo-2-[2-(2-methoxyethoxy)ethoxy]ethane (S1), respectively. In parallel, 5-tert-butylindole (2-tBu) and 5-chloroindole (2-Cl) were also prepared from their respective 4-substituted hydrazine hydrochlorides via Fisher indole synthesis (Scheme 2 in FIG. 2). For the 2-Cl, sulfuric acid was added to expedite the slow reaction, otherwise the HCl inherent to the hydrazine salts was sufficient to catalyze the reaction. The 5-substituted indoles were N-alkylated to the corresponding [(3-acetoxy)propyl]indolinium iodide derivatives by heating to 100° C. in neat, freshly prepared 3-iodopropyl acetate S2 (Scheme 3 in FIG. 2), providing good to nearly quantitative yields.

Figure 3:
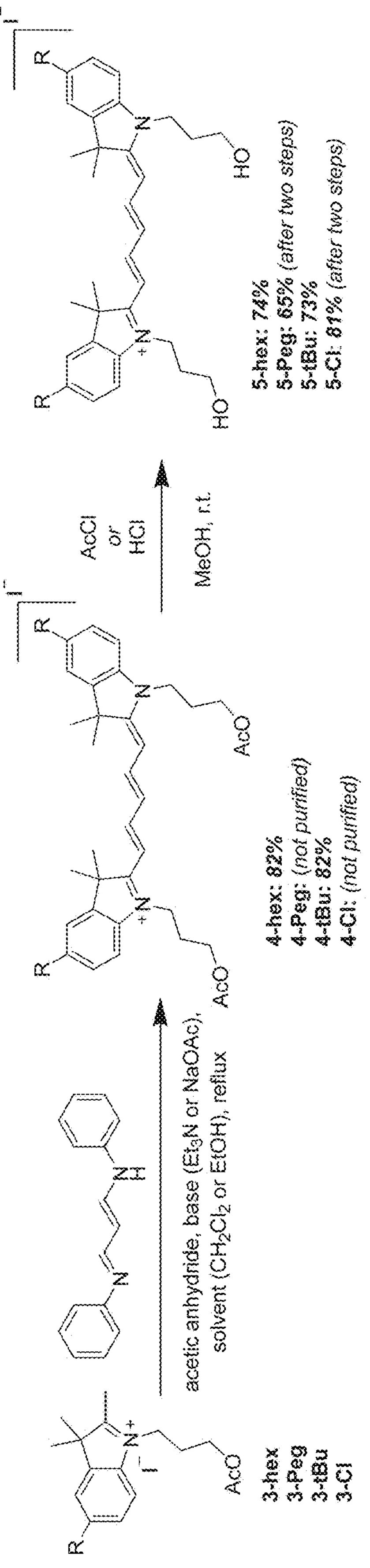
FIG. 3 shows synthetic Scheme 4 for the synthesis of N,N-bis(3-hydroxypropyl)dicarboindocyanines. Individual procedures vary slightly for each cyanine depicted in this scheme; details can be found in the Appendix. Yields indicated for each step (italicized bold) following compound number. Corresponding NMR spectra and mass spectra of all products are shown the Appendix in the order of appearance.
Figure 4:
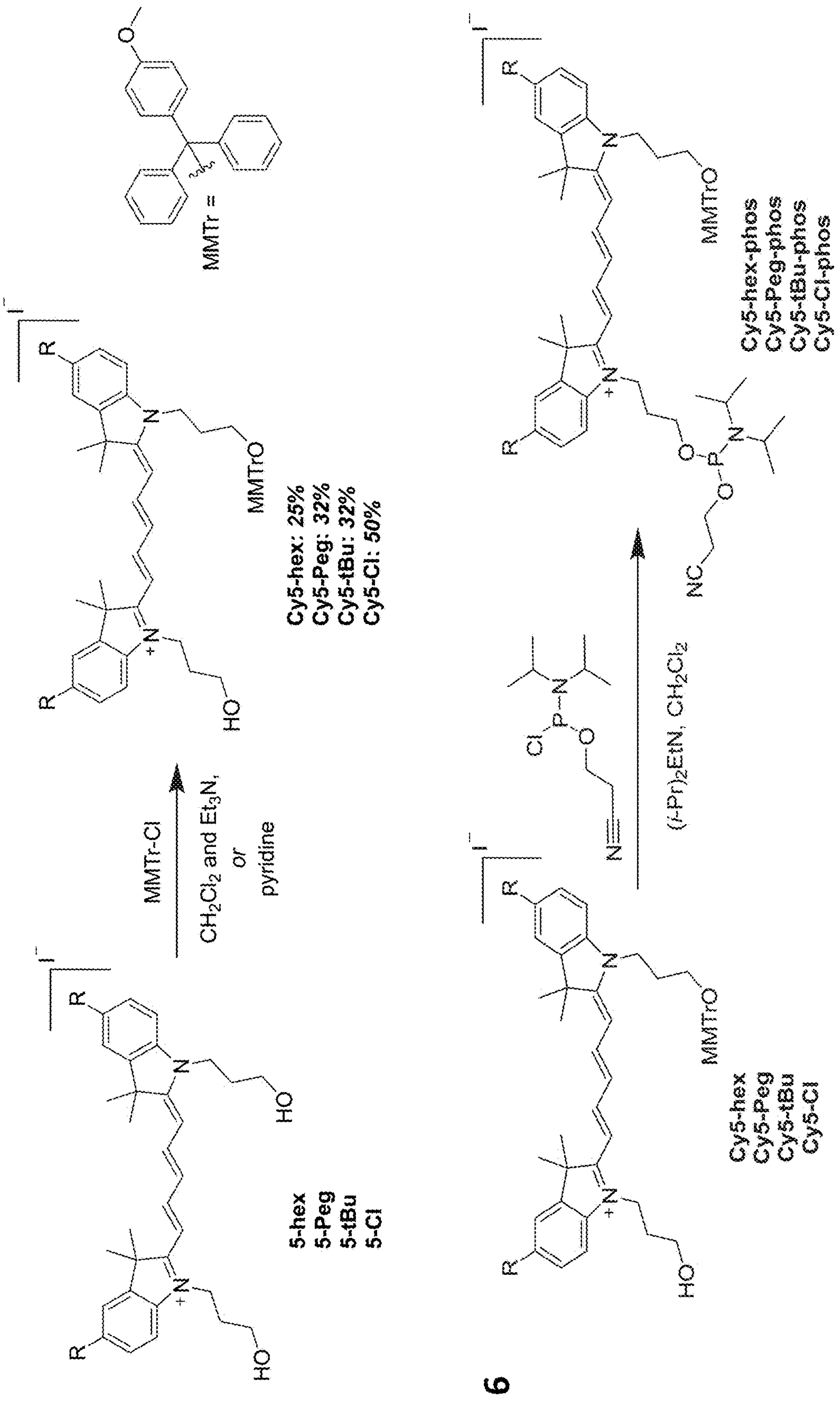
FIG. 4 depicts synthetic Schemes 5 and 6 for the preparation of final cyanine dye derivatives for internal incorporation into DNA during synthesis. Scheme 5 describes tritylation of the dicarboindocyanine series. Scheme 6 describes dicarboindocyanine phosphoramidite conversion. For the final step (Scheme 6), product yield was assumed to be quantitative based upon thin layer chromatography (TLC), after a quick purification, product was immediately re-solubilized in anhydrous acetonitrile under N2 gas in a reagent bottle and then installed into the DNA synthesizer for subsequent synthesis. Yields are shown (italicized bold) where determined, following compound number. Corresponding NMR spectra and mass spectra are shown in the Appendix in the order of appearance

Next, the series of indolinium iodide salts were coupled with malonaldehyde dianilide hydrochloride to form N,N-bis(3-acetoxypropyl)dicarboindocyanine derivatives (Scheme 4 shown in FIG. 3). Although the solvent and base varied dependent upon availability at the given time, yields were comparable nonetheless. Subsequently, the acetoxy groups were deprotected by either HCl or acetyl chloride in the presence of methanol to obtain the N,N-bis(3-hydroxypropyl)dicarboindocyanine series. In the cases of 4-hex and 4-tBu, purification was carried out prior to hydrolysis, while 4-Peg and 4-Cl were hydrolyzed as crude materials. The final, stable dyes (monomethoxytrityl substituted Cy5 derivatives, Scheme 5 in FIG. 4) were then prepared by the substitution reaction of the terminal hydroxyl group with 4-monomethoxytrityl chloride (MMTr-Cl). Due to the statistical nature of this substitution, both mono- and bis-tritylation occurs, and the separation of the two is non-trivial. Sacrificing target yield (32% and below) by using excess Cy5 significantly limited formation of the bis-trityl byproduct while also making subsequent purification much more facile. Furthermore, any unreacted bis-hydroxy cyanine was simply recovered and reused, as opposed to that of a bis-trityl byproduct, which would require additional hydrolysis for its recycling. While the 4,4'-dimethoxytrityl (DMTr) group is more common as the protective group of primary alcohols when used for DNA synthesis, this protective group is less robust (the DMTr structure is shown in Appendix Figure S1). Thus, the more stable 4-monomethoxytrityl (MMTr) group was used to protect the primary alcohol in this work. Importantly, exchanging the DMTr with the MMTr group does not impact the automated DNA synthesis protocol and had no apparent effect on overall yields. Finally, the MMTr protected cyanine derivatives were each coupled with 2-cyanoethyl N,N-diisopropylchlorophosphoramidite to yield dicarboindocyanine phosphoramidites (Scheme 6 in FIG. 4). Once prepared, the Cy5-phosphoramidites were purified then immediately dried down. Initial successful Cy5-phosphoramidite syntheses were confirmed by the presence of 31P NMR resonances in the range of 140-150 ppm, however, TLC provided sufficient confirmation of product for later trials. Additionally, the scale of the reactions was modified such that all phosphoramidite could be consumed by the DNA synthesizer within two days. Once thoroughly dried, the phosphoramidite samples were reconstituted in dry acetonitrile and immediately used for DNA synthesis.

Two factors appear particularly important for successful DNA synthesis trials in preparation of the final phosphoramidites. The first was the use of iodide salts. The iodide salts, as opposed to the more commonly found commercial Cy5-phosphoramidite chloride salts, have improved solubility and a larger retention factor, making their synthesis easier to monitor by TLC. Comparatively, the chloride salts required a much more protic TLC eluent (methanol/dichloromethane as opposed to acetonitrile/dichloromethane), which additionally undergoes substitution on the phosphoramidite moiety complicating TLC interpretation. The second factor relates to purification. During initial, poor-yielding DNA synthesis trials, it was difficult to purify the Cy5-phosphoramidites in a timely manner prior to placing the samples into the DNA synthesizer. Concentrating the Cy5-phosphoramidite reaction crude, in an attempt to go directly to column chromatography, resulted in significant decomposition of the crude product presumably due to the presence of acid when the amine was evaporated. This decomposition was circumvented by washing with saturated sodium bicarbonate. However, the bicarbonate wash converted the excess 2-cyanoethyl N,N-diisopropylchlorophoramidite to cyanoethyl-N,N-diisopropyl-H-phosphonamidate (see Figure S2 for structure, characterization data available in Appendix), that undesirably co-eluted with Cy5-phosphoramidites during column chromatography. The molar equivalent quantity of 2-cyanoethyl N,N-diisopropylchlorophoramidite was not reduced, as some amount is inevitably consumed by moisture in the reaction solvent, despite best efforts to dry the solvent over activated 3 Å molecular sieves. Ultimately, the impurity was removed through iterative powderization (see below for General Procedure for Cy5-phosphoramidite Synthesis), tracking its removal through TLC upon staining with ninhydrin (impurity shows bright red-orange upon heating the stained TLC); this resulted in significantly improved yields for DNA synthesis. As described below, the iterative powderization involved adding solvent to the crude product and then stripping a portion of it away, so that the supernatant retains one or more impurities while the target compound precipitates. It is critical that the solvent the product is soluble in (for example, dichloromethane) has a lower boiling point than the solvent that the product is essentially insoluble in (for example, hexane). This process is repeated until reaching the desired purity.

DNA Synthesis, Oligonucleotide Purification, and Overall Yield

Five different DNA oligonucleotide sequences were subsequently synthesized using each new Cy5 dye analog, incorporating the dye internally during automated synthesis. Full sequences with the dye insertion locations are listed in Table 1. These sequences are the same as the four Holliday junction (HJ) sequences described previously (see refs. 11, 13, 4, and 18) with the addition of a further direct complement to the HJA sequence, designated as HJAcomp. Each sequence was synthesized in multiple copies with at least 3 and up to 8 replicates at 1 μmole scale.

TABLE 1

DNA Sequences

| Designation | Oligonucleotide sequence (5'-3') | $T_m$ |
|---|---|---|
| HJA | ATATAATCGCTCG-**X**-CATATTATGACTG (SEQ ID No: 1) | 64.4 |
| HJB | CAGTCATAATATG-**X**-TGGAATGTGAGTG (SEQ ID No: 2) | 64.7 |

TABLE 1-continued

| DNA Sequences | | |
|---|---|---|
| Designation | Oligonucleotide sequence (5'-3') | $T_m$ |
| HJC | CACTCACATTCCA-**X**-CTCAACACCACAA (SEQ ID No: 3) | 69.4 |
| HJD | TTGTGGTGTTGAG-**X**-CGAGCGATTATAT (SEQ ID No: 4) | 69.1 |
| HJAcomp | CAGTCATAATATG-**X**-CGAGCGATTATAT (SEQ ID No: 5) | 64.4 |

In Table 1, X denotes site of Cy5 analog incorporation. $T_m$ is the melting temperature determined using the OligoAnalyzer Tool of Integrated DNA Technologies with Cy5 inserted into each oligo at the X position.

DNA synthesis utilized an automated Applied Biosystems Expedite 8909 DNA Oligo Synthesizer (supplied by Biolytic Lab Performance, Inc., Fremont, CA) using solid phase phosphoramidite coupling chemistry carried out at 1 μmole scale on controlled-pore glass (CPG) columns that contained the initial 3' starting base in protected form. DNA oligos were synthesized following the instrument's standard coupling protocols, with the exception of the Cy5-phosphoramidite insertion step. For coupling of the Cy5 analog phosphoramidites (monomer for these purposes), the coupling time was modified such that three pulses of monomer and activator (Act, 0.25 M 5-ethylthio-1H-tetrazole in anhydrous acetonitrile) were pushed into the column by flushing 9-10 pulses (optimized based on the volume of the tubing from the monomer reservoir to the synthesis column) of acetonitrile wash immediately after. The monomer and activator was then allowed to react with the column by flushing 7 pulses of wash over the course of 150 seconds. Next, the unreacted monomer and activator was rapidly flushed out of the column using 8 pulses of wash. The entire process was repeated three times to achieve a total of 9 pulses of monomer and activator per coupling. The end of the coupling was the same as the standard protocol, which included additional activator and wash steps. Appendix Section 4 provides more information on the standard coupling protocols.

All solutions and reagents used with the system were purchased from Glen Research (Sterling, VA) and used in accordance with their instructions and that of the DNA synthesizer. Once synthesized, the crude DNA sequences still attached to the CPG columns were stored at 4° C. in the dark until a sufficient number of synthetic replicates had been collected (20+) for bulk processing in parallel. The latter began with ammonolysis where the individual CPG columns used on the DNA synthesizer were opened, the CPG removed to new tubes and the contents shaken under 7% $NH_4OH$ (aq.) for one week at room temperature. Ammonolysis both frees the DNA sequences from the CPG beads and deprotects the individual nucleobases, but it can also lead to cleavage of the cyanines. Thus, conditions were carefully optimized to reach the 7% $NH_4OH$ used here from the original manufacturer suggestion of 30%, where lower concentrations resulted in poor partial deprotection reactions while higher concentrations lead to rapid degradation of the cyanines, particularly the electron deficient Cy5-Cl containing sequences; these required the further precaution of decreasing the ammonolysis reaction time to 48 hours. Upon completion of the ammonolysis, the crude oligo solution underwent salt exchange (see Salt Exchange of DNA Sequences below for the procedure) using triethylammonium acetate (TEAA) buffer followed by deionized water, and were then concentrated to dryness. This buffer exchange is critical as concentration of the sequences directly from basic solution leads to nearly complete decomposition of the cyanines. Dried crude samples can be stored long term at −20° C. if desired.

Desalted oligo solutions were then analyzed by liquid chromatography-mass spectrometry (LCMS, see Characterization below for more detail) to confirm the presence of correct sequence in the crude product. Samples containing the confirmed dye-labeled DNA sequences were then pooled and purified by preparatory scale reverse phase HPLC (2707 Autosampler, 2545 Quaternary Gradient Module, 2998 Photodiode Array Detector, and Fraction Collector III, Waters, Inc, Milford, MA) using an XBridge OST $C_{18}$ OBD 19×50 mm column (Part No. 186008962, Waters, Inc, Milford, MA) with a gradient of increasing methanol in 0.1 M TEAA (aq.). For Cy5-hex, Cy5-Peg and Cy5-tBu containing sequences, LC fractions were concentrated to dryness directly from the 0.1 M TEAA buffer/methanol solution. In the case of Cy5-Cl containing oligos, individual LC fractions were again subjected to salt exchange to remove the excess buffer, as the direct concentration from TEAA solution resulted in nontrivial (10-20%) decomposition. Dried LC fractions were reconstituted in small volumes of water (Optima Grade), to keep concentration sufficiently high (25-50 μM) to visualize and separate low percentage impurities on LCMS. Purified fractions were combined, concentrated, then re-analyzed via LCMS for a final purity assessment.

The predicted and observed masses (as M/Z) for each dye containing sequence can be found in Appendix Table S2. The primary impurity observed closely follows the target sequence in reverse phase chromatography and cannot be fully separated; it was identified in each case as the target sequence missing the last nucleobase (denoted as N-1 sequences). For the Cy5-Cl sequences, there was also an impurity present (1-2%) in all cases which precedes the target band during reverse phase chromatography, it was identified as the half target sequence in which the Cy5-Cl had been hydrolyzed (absorption band is observed centered at approximate 430 nm). Final materials were accepted when they achieved greater than 90% purity, with an average sample purity of 95%. Overall, the final yields varied from 5- up to 24.3% (Table 3, based on an expected maximum yield of 1 μmole per CPG column at this synthetic scale). The large deviations are due in part to the time a particular sequence was synthesized during a given dye-analog's in use or useful reagent lifetime (e.g., synthesis number 10 from a given Cy5-phosphoramidite sample versus synthesis number 1 will inherently exhibit lower yield due to degradation of the Cy5-phosphoramidite over time). Another factor contributing to overall yield was the varying levels of difficulty with purification encountered, which was found to be both dye and sequence dependent.

Dye Properties

Due to the overall poor solubility of the parent cyanine dye derivatives in water, the octanol-water partition coefficient (log P) could not be determined by the traditional “shake flask” method. In lieu of this approach, modelling software developed by Advanced Chemistry Development, Inc. was used to predict the partition coefficient and solubility in water (log S0), as shown in Table 2. As an additional means of comparison with direct relevance to the final intended utility of these oligos, the average concentration of methanol required to elute the DNA sequences containing the given dye from the reverse phase HPLC column was determined (the greater the methanol content required to elute, the more hydrophobic the dye). The DNA-dye sequences were utilized for this instead of the free dyes because they are capable of eluting at lower methanol content, but the hydrophobic character of the dye still dominates the elution profile. The calculated log P and log S0 values suggest that the order of increasing hydrophobicity, according to functional group, is as follows: Peg<Cl<<tBu<<hex. This is in close agreement with the relative “stickiness” of the DNA-dye sequences towards Cis stationary phase. The slightly greater methanol content required to elute Cy5-Peg containing sequences relative to Cy5-Cl can be attributed to the amphiphilic nature of the Peg chains, where the increased number of hydrogen bond-accepting O atoms favor interaction with the aqueous phase. This tendency is, however, offset by the increased number of C—H bonds, which promote interaction with the hydrophobic phase.

along with moderate Stokes shifts suggest that the peripheral substituents used in the present study have only minimal effect on the excited-state structural relaxation relative to the ground-state conformation for each Cy5 derivative. The Cy5-Peg and Cy5-hex have broader absorption spectra than the other two derivatives. The fluorescence QY ($\Phi_F$) and the excited state fluorescence lifetimes ($\tau$) of these dyes follow an inverse trend as a function of the absorption peak maxima, where the weaker the electron donating character of the 5,5' substituents—the larger the $\Phi_F$ exhibited. Thus, the largest determined $\Phi_F$ was 0.27 for Cy5-Cl, decreasing to 0.21 for Cy5-tBu, and decreasing further to 0.07 for Cy5-hex and Cy5-Peg. Corresponding $\tau$ values ranged from 0.42 up to 1.11 ns and appeared to consist predominantly of a single exponential decay. In addition, $\Phi_F$ for 4-hex and 4-tBu were determined (not shown) and found to be identical to those of Cy5-hex and Cy5-tBu, respectively, indicating that the position of the hydroxyl substituents on the indolenine groups did not influence the measurements.

Photophysical Properties of the Dye-Labeled Oligonucleotides

Table 3 (proved in FIG. 7) summarizes the absorption and emission properties of the twenty novel Cy5 containing DNA sequences in neat $H_2O$. The corresponding absorption and emission spectra collected from each of the single stranded (ss) oligonucleotide are presented in FIGS. 6A-6H. For comparative purposes, the properties of unsubstituted Cy5 oligonucleotides (R═H) are summarized in Appendix Table S3. As used herein, “Cy5-x”refers to the given labeled oligonucleotide. Upon incorporation into DNA, the absorption maxima measured in water for these Cy5 derivatives are identical or slightly red shifted (0-3 nm for Cy5-hex, 2-6 nm for Cy5-Peg, 2-5 nm for Cy5-tBu and 5-8 nm for the Cy5-Cl oligos), compared to the parent dyes measured in methanol. The wavelength maxima vary within 1-4 nm on a sequence-to-sequence basis within each HJ-Cy5 series and there is no discernable trend as to which HJ sequence produces the greatest bathochromic shift. For example, the HJC-Cy5-Cl is close to the most red-shifted of its series, while the HJC-Cy5-Peg is the most blue-shifted of its series. The incorporation of the various Cy5 analogs does not significantly influence the shape of the DNA absorption band in any case. Since the DNA and Cy5 analog absorbance behaved independently, the molar absorptivity ($\varepsilon$, $M^{-1}\cdot cm^{-1}$) of the Cy5 analog in each sequence was determined based on the calculated absorbance of the DNA at 260 nm. This was accomplished using the nearest-neighbor approximation and assumed that the percent contribution of the Cy5 analog at 260 nm was constant between the parent Cy5 in methanol

TABLE 2

Dye properties

| Dye | Log P | Log S0 | Av. % MeOH for DNA-dye elution | $\lambda_{max\ abs}$ (nm) | $\lambda_{max\ em}$ (nm) | Stokes Shift ($cm^{-1}$) | $\Phi_F$ | $\tau$ (ns) |
|---|---|---|---|---|---|---|---|---|
| Cy5-hex | 5.66 | −9.94 | 51 | 670 | 699 | 619 | 0.07 | 0.42 |
| Cy5-Peg | 1.58 | −7.88 | 31.5 | 668 | 693 | 540 | 0.07 | 0.44 |
| Cy5-tBu | 3.43 | −8.25 | 41 | 654 | 678 | 541 | 0.21 | 0.94 |
| Cy5-Cl | 2.35 | −7.94 | 30.5 | 648 | 670 | 507 | 0.27 | 1.11 |
| Cy5[1] | 1.73 | −6.25 | 30.0 | — | — | — | — | — |

[1]Cy5 refers to the unsubstituted Cy5. For some comparative values of this dye as incorporated into DNA see Table S2. Absorption and emission properties determined in methanol. QY ($\Phi_F$) determined against 5,10,15,20-tetraphenylporphyrin standard ($\Phi_F$ = 0.07 in toluene).

[50] Acetate functionalized cyanines (4) were utilized for the log S0, log P as this more closely matches the cyanine structure once imbedded within DNA. Log P and log S0 determined using the Molecular Property Calculations on the Percepta Platform from Advanced Chemistry Development, Inc. (Toronto, Canada). Average % methanol for DNA-dye elution based on elution time for each sequence (HJA-D and HJAcomp) containing the indicated dye.

Figure 5B:
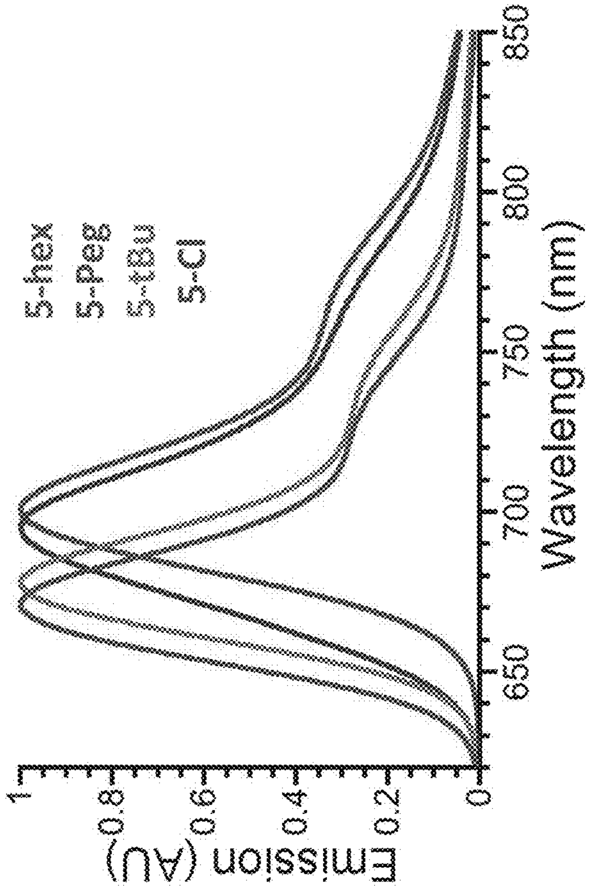
FIGS. 5A and 5B represent the absorption and emission spectra for the as-synthesized dye series.
Figure 5A:
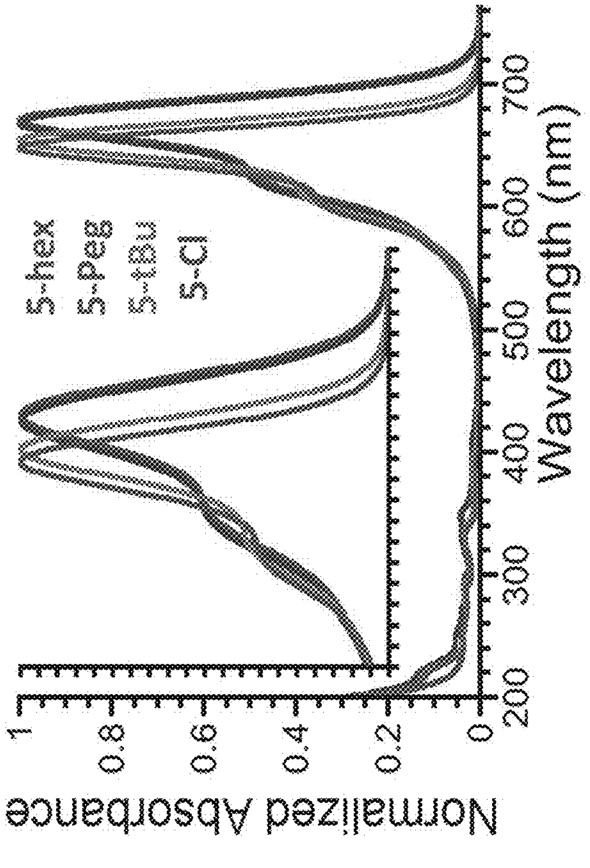
Figure 6:
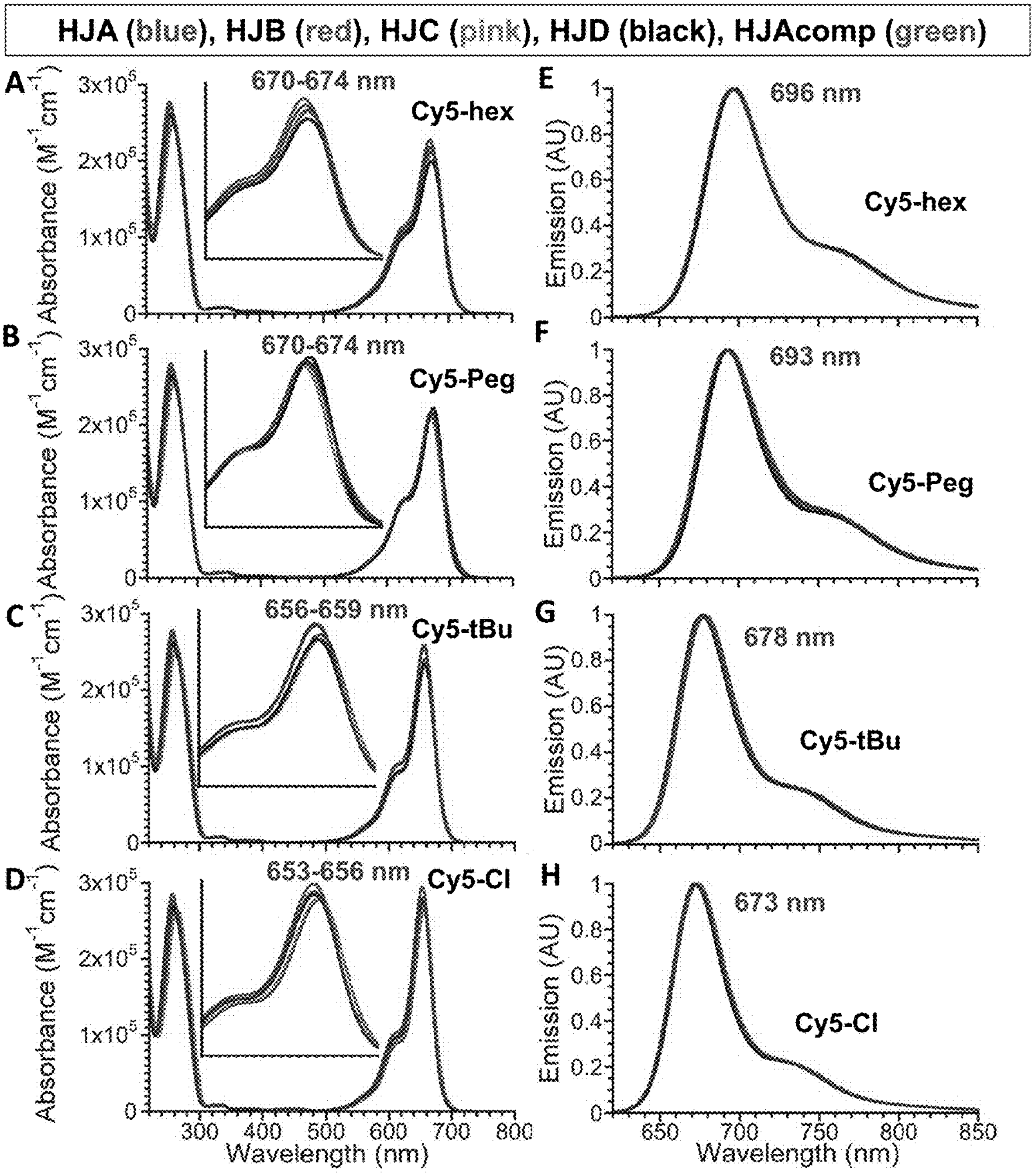
FIGS. 6A through 6H show absorption and emission spectra for the Cy5 dye series incorporated into 5 DNA oligonucleotides (Table 1). Absorption spectra of the Cy5-hex (A), Cy5-Peg (B), Cy5-tBu (C), and Cy5-Cl (D) containing DNA sequences acquired in neat water at 4-5 μM. Inset highlights the range of observed absorption maxima as also indicated in purple. Corresponding normalized emission spectra for Cy5-hex (E), Cy5-Peg (F), Cy5-tBu (G), and Cy5-Cl (H) acquired in neat water at a concentration of 0.4-0.5 μM. For emission, samples were excited at 600 nm and spectra collected from 620 to 850 nm. Averaged emission maxima are shown in purple.
Figure 8:
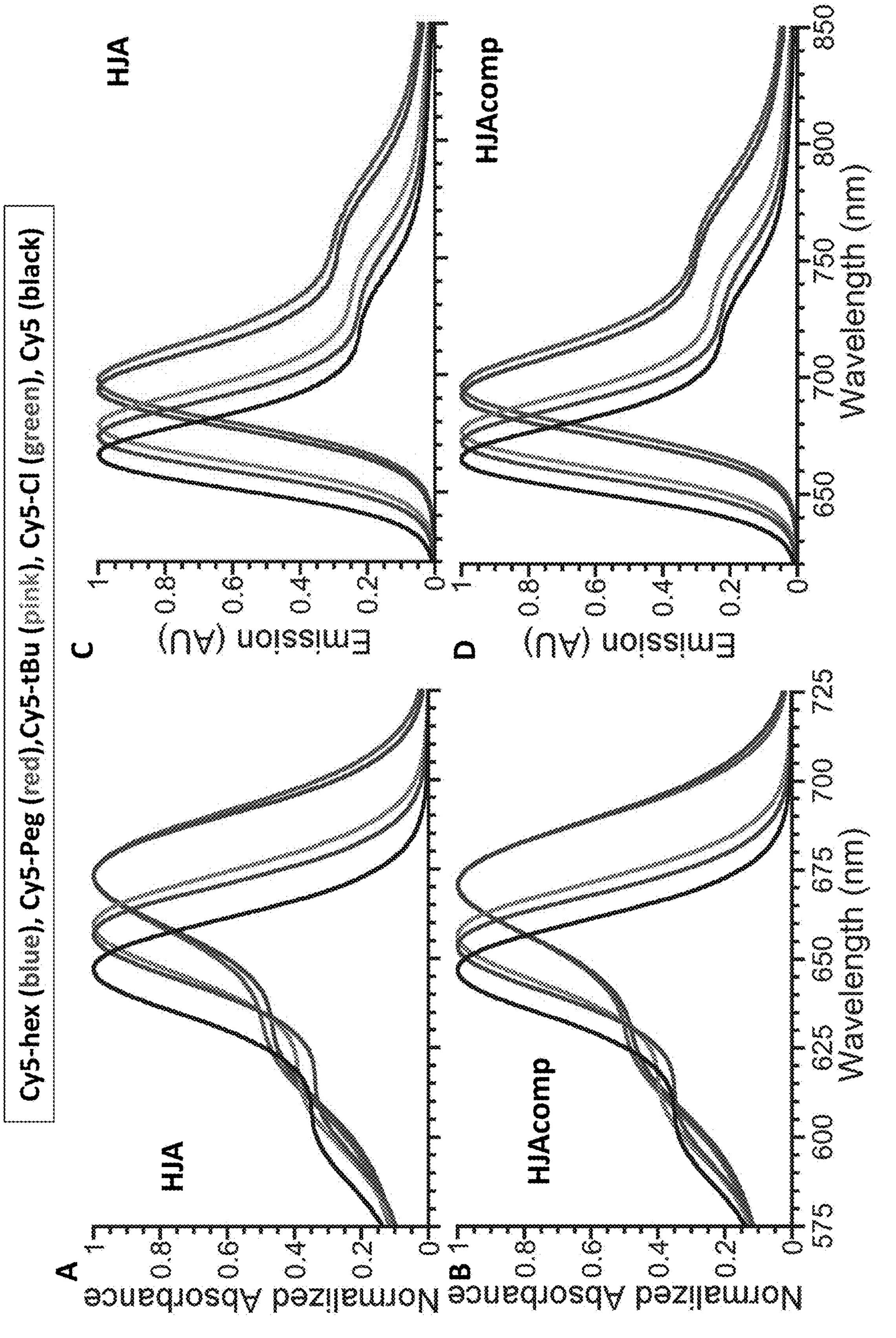
FIGS. 8A through 8D depict absorption and emission spectra for select Cy5 dye series DNA oligonucleotides. Normalized absorption spectra of the HJA (A) and the HJAcomp (B) sequences incorporating Cy5-hex Cy5-Peg, Cy5-tBu, Cy5-Cl and Cy5 dye acquired in neat water at a concentration of 4-5 μM. Corresponding normalized emission spectra for the HJA (C) and the HJAcomp (D) sequences acquired in neat water at a concentration of 0.4-0.5 μM. For emission, samples were excited at 600 nm and spectra collected from 620 to 850 nm.

Relative absorption and emission properties of the novel cyanine dyes are also summarized in Table 2. The table includes data acquired for those possessing pendant hydroxyl substituents (5), as the diacetoxy cyanines (4) were not cleanly isolated in all cases. FIGS. 5A and 5B show the normalized absorption and emission spectra of the cyanines, respectively, as acquired in methanol. Here, the wavelength of maximum absorbance shifts with respect to electron withdrawing/donating character of the 5,5' substituents, spanning the window of 648-670 nm. The greater the electron donating character, the greater the bathochromic shift, and vice versa. Thus, the order of increasing shift of the absorbance maxima is: Cy5-Cl<Cy5-tBu<Cy5-Peg≈Cy5-hex. The emission maxima of this series, spanning 670-699 nm, follows the same order with each Cy5 possessing a moderate Stokes shift in the range of 507-619 $cm^{-1}$. The mirroring of absorption and fluorescence spectra and the DNA-incorporated Cy5 analog in water. Thus, the ε at 260 nm values found in Table 3 are the sum of the calculated value and the Cy5 analog contribution. For Cy5 analogs incorporated into sequences, the molar absorptivity at wavelength of maximum absorbance ($\varepsilon_{Cy5}$) fall within a narrow window for each DNA-dye series: 200,900-219,800 ($M^{-1}\cdot cm^{-1}$) for Cy5-hex sequences, 209,500-221,400 ($M^{-1}\cdot cm^{-1}$) for Cy5-Peg sequences, 249,300-269,600 ($M^{-1}\cdot cm^{-1}$) for Cy5-tBu sequences, and 269,300-288,400 ($M^{-1}\cdot cm^{-1}$) for the Cy5-Cl sequences. The deviation of $\varepsilon_{Cy5}$ between sequences, and also within the same series of a given dye, is likely due to small differences in microenvironments and their relative purities. The significantly lower $\varepsilon_{Cy5}$ (~20% average decrease) observed for Cy5-hex and Cy5-Peg is attributed to the increased width of the collective vibronic absorption bands ($A_{0-0}$ and $A_{0-1}$) relative to those of Cy5-tBu and Cy5-Cl. Because the $A_{0-0}$ and $A_{0-1}$ vibronic bands begin to overlap before the $A_{0-0}$ falls below 50% maximum intensity, the full-width-at-half-maximum (FWHM) could not be determined, but the relative broadness can nonetheless be seen in FIGS. 6A-6H.

The emission maxima observed in the DNA-Cy5 analog sequences parallel the trend observed for the unincorporated dyes—the order of shortest to longest wavelength emitting dye does not change and the Stokes' shifts remain in a similarly moderate range. As with the absorption maxima, the emission maxima vary slightly on a per-sequence basis, and the specific sequence with the greatest bathochromic shift within each series is dye and sequence dependent. As shown in Table 3, the fluorescence QY's in the HJ Cy5-hex series are the weakest of all sequences studied, ranging from 0.07-0.09, followed closely by the HJ Cy5-Peg series (0.09-0.10). The QY values of the HJ Cy5-tBu series is next in the range of 0.20-0.26 and the largest fluorescence QY's belong to the HJ Cy5-Cl series ranging from 0.27-0.37. On a per dye basis, these results, as anticipated, parallel those of the non-DNA-conjugated parent dyes. In all cases, the fluorescence QYs of DNA-incorporated Cy5s are either unchanged, or slightly enhanced relative to those of the parent dyes. For the HJ Cy5-Peg series, QY as a whole increases between 29-43%, for the remaining series only HJA and HJC exhibit enhanced emission. For the HJA/C Cy5-hex series, the increase is 14-29%, for the HJA/C Cy5-tBu the increase is 24%, and for the HJA/C Cy5-Cl, an increase of 30-37% is seen.

The average excited-state fluorescence lifetimes ($\tau_{avg}$) along with the corresponding radiative and non-radiative rate constants for the substituted Cy5 labeled DNA oligos are also presented in Table 3. In contrast to the free substituted Cy5 dyes in methanol, the fluorescence decays of the dyes incorporated into DNA were generally found to be non-exponential and well fit by a biexponential decay function. This observation suggests that the substituted Cy5 dyes assume multiple configurations in the excited state when attached to DNA strands in the aqueous environment. Similar to the free dyes in methanol, the $\tau_{avg}$ increases in the order of Cy5-hex<Cy5-Peg<Cy5-tBu<Cy5-Cl. For each substituted Cy5, the $\tau_{avg}$ depends on the particular DNA sequence. The variation in $\tau_{avg}$ with DNA sequence is greatest for the Cy5-tBu and Cy5-Cl series, where the longest and shortest fluorescence lifetimes differ by as much as 26%. The radiative rate for each substituted Cy5 DNA oligo is estimated from:

$$k_{rad} = \frac{\phi_F}{\tau_{avg}}, \qquad \text{(Eq. 1)}$$

where $\Phi_F$ is the fluorescence QY, and results in the trend $k_{rad,Cy5\text{-}hex} \sim k_{rad,Cy5\text{-}Peg} < k_{rad,Cy5\text{-}Cl} \sim k_{rad,Cy5\text{-}tBu}$. Thus, the red-shifted Cy5-hex and Cy5-Peg oligos, which have relatively broad absorption bands, generally show smaller radiative rates than the Cy5-Cl and Cy5-tBu labeled oligos. The radiative rate was also found to be dependent on the DNA sequence for each substituted Cy5. The radiative rate for both cyanine dyes, and also other dyes, has been observed to depend on the environment surrounding the dye. The non-radiative rate is determined from:

$$k_{nr} = k_f - k_{rad}, \qquad \text{(Eq. 2)}$$

where $k_f = \tau_{avg}^{-1}$. The results in Table 3 show that $k_{nr}$ generally increases in the order $k_{nr,Cy5\text{-}Cl} < k_{nr,Cy5\text{-}tBu} < k_{nr,Cy5\text{-}Peg} < k_{nr,Cy5\text{-}hex}$, and there is variation in $k_{nr}$ with DNA sequence for each substituted Cy5. While the mechanism for the substantially larger $k_{nr}$ for Cy5-hex and Cy5-Peg is beyond the scope of this work, one possibility is that the electron donating hex and Peg substituents promote more cis-like ground state conformations that increase either the rate of photoisomerization or the rate of nonradiative decay directly to the ground state.

Analyses of the substituted dye solubility and hydrophobicity, as estimated from modeling and HPLC analysis, suggest that they are indeed demonstrating the physicochemical properties that were expected for each derivative. Even after undergoing conversion to the final phosphoramidite, exposure to all the highly reactive automated DNA chemistry reactions/environment, extended purification protocols with multiple harsh chemical treatments, and multiple HPLC procedures with subsequent concentration, the dye derivatives mostly maintained the photophysical properties of the parent dye in terms of excited state fluorescence lifetime and quantum yield.

Materials and Methods

Chemical Synthesis. Triphenylphosphine and 2-cyanoethyl N,N-diisopropylchlorophos-phoramidite (97%) were purchased from Acros Organics. 4-Methoxyphenylhydrazine hydrochloride (95%), malonaldehyde dianilide hydrochloride and triethyleneglycol monomethyl ether were purchased from TCI America. 3-Methyl-2-butanone (98%) and 3-chloropropyl acetate (98%) were purchased from Alfa Aesar. $CsCO_3$ (99.9%) was purchased from Chem-Impex International. 4-Methoxytriphenylmethyl chloride (4-monomethoxytrityl chloride, 97%) and 4-chlorophenylhydrazine hydrochloride (93%) were purchased from Oakwood Chemical. Hydrobromic acid (HBr, 48%), N-bromosuccinimide (99%), sodium iodide (NaI, 98%), triethylamine (99.5%), N,N-diisopropylethylamine (99.5%) and sulfuric acid ($H_2SO_4$, reagent grade, 95-98%) were purchased from Sigma Aldrich. Bulk chromatography solvents were purchased from Pharmco/Greenfield Global. All the other chemicals, including reaction solvents were purchased from Millipore-Sigma or Fisher Scientific and used as received, except for $CH_2Cl_2$, $CH_3CN$ and N,N-diisopropylethylamine, which were dried over freshly activated 3 Å molecular sieves (Sigma Aldrich) before use for phosphoramidite coupling reaction. For the commercial Cy5 dye, we used commercially available, unsubstituted Cy5-H (R═H) as the standard for comparison of the DNA-Cy5 sequences. Standard sequences were prepared by automated DNA synthesis in the same manner using the commercially available Cy5 phosphoramidite 1-[3-(4-monomethoxytrityloxy)propyl]-1'-[3-[(2-cyanoethyl)-(N,N-diisopropylphosphoramidityl]propyl]-3,3,3',3'-tetramethylindodicarbocyanine chloride (Glen Research, Sterling VA).

Characterization. $^{1}H$ and $^{13}C$ NMR spectra were recorded on a Bruker SpectroSpin or Bruker Ascend 400 MHz spectrometer (Bruker Corporation, Billerica, MA). Chemical shifts for $^{1}H$ NMR spectra are reported relative to tetramethylsilane (TMS) signal in deuterated solvent (TMS, δ=0.00 ppm). All J values are reported in hertz. Chemical shifts for $^{13}C$ NMR spectra are reported relative to deuterated chloroform ($CDCl_3$) signal (δ=77.16 ppm) or DMSO-$d_6$ (δ=2.52 ppm) in the case of 5-tBu. Mass spectral analysis for both small molecules and DNA oligos was performed using an ACQUITY UPLC system equipped with a single quadrupole (SQD2) mass detector (Waters, Inc, Milford, MA) as described in references 58-59. Additionally, purity of the DNA oligos was assessed on the ACQUITY UPLC using the photodiode array detector (PDA eλ Detector) and fluorescence detector (FLR Detector) modules. All LCMS samples were injected from Fisherbrand Optima Grade Solvents; $MeOH/H_2O$ (1/1) for small molecules and neat $H_2O$ for DNA oligos, then eluted using an increasing gradient of methanol in aqueous 0.05M triethylammonium acetate buffer (pH 7.0). For small molecules, Waters BEH $C_{18}$ column (Part No. 186002350) was utilized, and for DNA sequences Waters Oligonucleotide BEH $C_{18}$ column (Part No. 186003949) was utilized. Absorption spectra were recorded using a Cary 60 UV-Vis (Agilent Technologies, Inc., Santa Clara, CA) and fluorescence spectra were recorded using a FluoroMax-4 Spectrofluorometer (Horiba Scientific, Piscataway, NJ). Fluorescence quantum yields (QYs) were determined against 5,10,15,20-tetraphenylporphyrin (TPP) standard ($\Phi_F$=0.07 in toluene), with common excitation at 600 nm. TPP standard was purchased from Frontier Specialty Chemicals (Logan, UT) then oxidized with 2,3-dichloro-5,6-cyano-p-benzoquinone (DDQ) to remove the stated 1-3% chlorin impurity. TPP was cross-referenced against oxazine 720 perchlorate (Luxottica-Exciton, Lockbourne, OH, $\Phi_F$=0.63 in MeOH), upon excitation at 580 nm with agreement of ±5%. The obtained fluorescence spectra were corrected for wavelength dependent instrumental sensitivity. Excited state fluorescence lifetimes were collected using a system described in refs. 62-64.

Synthetic Procedures. Detailed descriptions for the synthesis of 5-methoxy-2,3,3-trimethylindolenine (1-OMe), 5-hydroxy-2,3,3-trimethylindolenine (2-OH), 5-n-hexyloxy-2,3,3-trimethylindolenine (2-hex), 5-{2-[2-(2-methoxyethoxy)ethoxy]ethoxy}-2,3,3-trimethylindolenine (2-Peg), 5-tert-butyl-2,3,3-trimethylindolenine (2-tBu), 5-chloro-2,3,3-trimethylindolenine (2-Cl), 1-[3-(acetoxy)propyl]-5-n-hexyloxy-2,3,3-trimethylindolinium iodide (3-hex), 1-[3-(acetoxy)propyl]-5-{2-[2-(2-methoxyethoxy)ethoxy]ethoxy}-2,3,3-trimethylindolinium iodide (3-Peg), 1-[3-(acetoxy)propyl]-5-tert-butyl-2,3,3-trimethylindolinium iodide (3-tBu), 5-chloro-1-[3-(acetoxy)propyl]-2,3,3-trimethylindolinium iodide (3-Cl), 1,1'-bis(3-acetoxypropyl)-5,5'-bis(n-hexyloxy)-3,3,3',3'-tetramethyldicarboindocyanine iodide (4-hex), 1,1'-bis(3-acetoxypropyl)-5,5'-bis(tert-butyl)-3,3,3',3'-tetramethyldicarboindocyanine iodide (4-tBu), 1,1'-bis(3-hydroxypropyl)-5,5'-bis(n-hexyloxy)-3,3,3',3'-tetramethyldicarboindocyanine iodide (5-hex), 1,1-bis(3-hydroxypropyl)-5,5'-bis{2-[2-(2-methoxyethoxy)ethoxy]ethoxy}-3,3,3',3'-tetramethyldicarboindocyanine iodide (5-Peg), 1,1'-bis(3-hydroxypropyl)-5,5'-bis(tert-butyl)-3,3,3',3'-tetramethyl-dicarboindocyanine iodide (5-tBu), 5,5'-dichloro-1,1'-bis(3-hydroxypropyl)-3,3,3',3'-tetramethyl-dicarboindocyanine iodide (5-Cl), 1-(3-hydroxypropyl)-1'-(3-monomethoxytritylpropyl)-5,5'-bis(n-hexyloxy)-3,3,3',3'-tetramethyl-dicarboindocyanine iodide (Cy5-hex), 1-(3-hydroxypropyl)-1'-(3-monomethoxytritylpropyl)-5,5'-bis{2-[2-(2-methoxyethoxy)ethoxy]ethoxy}-3,3,3',3'-tetramethyl-dicarboindocyanine iodide (Cy5-Peg), 1-(3-hydroxypropyl)-1'-(3-monomethoxytritylpropyl)-5,5'-bis(tert-butyl)-3,3,3',3'-tetramethyl-dicarboindocyanine iodide (Cy5-tBu), and 5,5'-dichloro-1-(3-hydroxypropyl)-1'-(3-monomethoxytritylpropyl)-tetramethyl-dicarboindocyanine iodide (Cy5-Cl) are provided in the Appendix of U.S. Provisional Patent Application No. 63/307,328 filed Feb. 7, 2022 (hereinafter, "Appendix") which is incorporated herein by reference in its entirety.

General Procedure for Cy5-phosphoramidite Synthesis. In preparation for the reaction, an oven dried round bottom flask was charged with each MMTr-Cy5 iodide derivative (5, 0.16 mmol) then co-evaporated with dry $CH_3CN$ (3 times), and dried under vacuum for 2-8 h. At the time of reaction, the pre-charged vessel was filled with dry nitrogen, then dissolved in dried $CH_2Cl_2$ (3.2 mL) and treated with dried N,N-diisopropylethylamine (170 μL, 0.96 mmol). Then 2-cyanoethyl N,N-diisopropylchlorophosphoramidite (110 μL, 0.48 mmol) was transferred from the glove-box directly to the reaction solution. The reaction mixture was vigorously stirred at room temperature in the dark for 30 min under $N_2$. The reaction completion was assessed by TLC, then the solution was washed with saturated aqueous $NaHCO_3$ solution (2 times). The organic layer was dried over $Na_2SO_4$, filtered, and concentrated. The crude product was then dried under vacuum for 30 min to ensure all volatiles are removed before proceeding. Crude product was then dissolved in dry $CH_2Cl_2$ (~1 mL) and dry hexane (2~3 mL) was added to the solution for iterative powderization. The solvent was then slowly stripped on a rotary evaporator until the majority of the product precipitated, then the yellow-green colored supernatant was discarded. This procedure was repeated until the byproducts are no longer visible on TLC and the supernatant was the blue color of Cy5. The product is then coevaporated with dry $CH_3CN$ (3 times) and dried under vacuum for 30 min. Following this, the product was immediately used for DNA synthesis by resolubilizing to a concentration of 80 mM in anhydrous acetonitrile, transferring directly to a reagent bottle, which was then attached to the DNA synthesizer, priming the bottle lines, and starting the synthesis. See Appendix Section 4 for more information on the automated DNA synthesis coupling protocols.

Salt Exchange of DNA Sequences. Salt exchange was performed on each DNA sequence following the ammonolysis step. To begin, a Glen-Pak DNA Purification Cartridge (Glen Research, Sterling, VA, catalog no. 60-5200) was wetted with 5 mL neat MeCN (HPLC grade), then flushed with 5 mL of 0.2 M TEAA (in 18Ω water). The DNA-dye sequence (constituted in ammonia solution) was then passed through the Glen-Pak column via 10 mL syringe 3-5 times. If blue color remains in the ammonia solution after several passes, the solution was retained and set aside. The Glen-Pak was then flushed/washed with 5 mL of 0.2M TEAA followed by 5 mL of neat 18Ω water. The Glen-Pak was next purged of residual water by plunging air until no droplets were observed. DNA-dye sequences were then collected into Eppendorf tube by eluting from Glen-Pak with ~1 mL of MeCN/water (80/20). If the original ammonia solution retained color, and was set aside, the Glen-Pak was reconstituted by flushing with 5 mL of 0.2 M TEAA, and the loading/washing/eluting process repeated. The second eluent of DNA-dye solution was combined with the first and then concentrated to dryness on a Speed-Vac SPD 1030 (ThermoFisher Scientific, Waltham, MA). DNA-dye sequences were purified to >95% using a Waters Prep LC 150 preparatory system, aliquoted, and dried down for storage at −20° C. in the dark until needed.

Advantages

The described Cy5-phosphoramidites with 5,5'-substituents can be used in tandem with current technology (for either based FRET applications or multiplexed imaging/labelling of complex samples) or as an attractive alternative that operates deeper within the red and near-infrared (NIR) biological window. The ability to adjust hydrophilicity/hydrophobicity also offers the ability to fine tune the dye-dye interactions within complex systems designed for excitonic delocalization.

Further advantages include the ability to tune absorption and emission maxima relative to commercial indodicarbocyanine phosphoramidite; achievability of improved emission signal-to-noise ratio within biological samples, by using those analogs with deeper red-NIR absorption and emission; the ability to incorporate any variety of 5,5'-O-alkyl substituents enables a predictable set of photophysical properties, while further altering the hydrophilicity/hydrophobicity of the dye. Moreover, synthetic methodology demonstrates it is facile to derivatize requisite precursors for tuning of hydrophilicity/hydrophobicity. Modification of hydrophobicity can facilitate aggregate formation, a key feature of systems being examined for excitonic delocalization. These dyes can also be used in the role of energy acceptor with commercial Cy5-phosphoramidites for synthesis of FRET based systems. The use of different substituents, such as chloro-, demonstrates the ability to fine tune absorption and emission maxima, enabling production of a series of dyes capable of serving as either energy donor or energy acceptor in FRET based systems.

Further Embodiments

Also contemplates are Cy5 derivatives as described above but where R is selected from the group consisting of consisting of —CF3 and —CN.

The above-described Cy5 derivatives could find applications such as coherent exciton devices, nanophotonics, and biosensing. DNA Holliday junction templates allow variations of dye combinations and precision dye positions can be rapidly assayed, as well as creating aggregates of dyes that could not be prepared (either due to excess or lack of solubility) through alternative means. Nucleic acid nanostructures could serve as valuable tools incorporating these derivatives.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Ernst, L. A.; Gupta, R. K.; Mujumdar, R. B.; Waggoner, A. S., Cyanine Dye Labeling Reagents for Sulfhydryl-Groups. *Cytometry* 1989, 10 (1), 3-10.
2. Mujumdar, R. B.; Ernst, L. A.; Mujumdar, S. R.; Lewis, C. J.; Waggoner, A. S., Cyanine Dye Labeling Reagents—Sulfoindocyanine Succinimidyl Esters. *Bioconjugate Chemistry* 1993, 4 (2), 105-111.
3. Gerowska, M.; Hall, L.; Richardson, J.; Shelbourne, M.; Brown, T., Efficient reverse click labeling of azide oligonucleotides with multiple alkynyl Cy-Dyes applied to the synthesis of HyBeacon probes for genetic analysis. *Tetrahedron* 2012, 68 (3), 857-864.
4. Holzhauser, C.; Berndl, S.; Menacher, E; Breunig, M.; Gopferich, A.; Wagenknecht, H. A., Synthesis and Optical Properties of Cyanine Dyes as Fluorescent DNA Base Substitutions for Live Cell Imaging. *European Journal of Organic Chemistry* 2010, 2010 (7), 1239-1248.
5. Massey, M.; Algar, W. R.; Krull, U. J., Fluorescence resonance energy transfer (FRET) for DNA biosensors: FRET pairs and Forster distances for various dye-DNA conjugates. *Analytica Chimica Acta* 2006, 568 (1-2), 181-189.
6. Medintz, I. L.; Mauro, J. M., Use of a cyanine dye as a reporter probe in reagentless maltose sensors based on *E-coli* maltose binding protein. *Analytical Letters* 2004, 37(2), 191-202.
7. Schobel, U.; Egelhaaf, H. J.; Brecht, A.; Oelkrug, D.; Gauglitz, G., New-donor-acceptor pair for fluorescent immunoassays by energy transfer. *Bioconjugate Chemistry* 1999, 10 (6), 1107-1114.
8. Buckhout-White, S.; Brown, C. W; Hastman, D. A.; Ancona, M. G.; Melinger, J. S.; Goldman, E. R.; Medintz, I. L., Expanding molecular logic capabilities in DNA-scaffolded multiFRET triads. *RSC Advances* 2016, 6 (100), 97587-97598.
9. Cunningham, P. D.; Spillmann, C. M.; Melinger, J. S.; Ancona, M. G.; Kim, Y. C.; Mathur, D.; Buckhout-White, S.; Goldman, E. R.; Medintz, I. L., Forster Resonance Energy Transfer in Linear DNA Multifluorophore Photonic Wires: Comparing Dual versus Split Rail Building Block Designs. *Advanced Optical Materials* 2022, 9 (21), 2170084.
10. Mathur, D.; Samanta, A.; Ancona, M. G.; Diaz, S. A.; Kim, Y. C.; Melinger, J. S.; Goldman, E. R.; Sadowski, J. P.; Ong, L. L.; Yin, P.; Medintz, I. L., Understanding Förster Resonance Energy Transfer in the Sheet Regime with DNA Brick-Based Dye Networks. *ACS Nano* 2021, 15, 16452-16468.
11. Cannon, B. L.; Kellis, D. L.; Patten, L. K.; Davis, P. H.; Lee, J.; Graugnard, E.; Yurke, B.; Knowlton, W. B., Coherent Exciton Delocalization in a Two-State DNA-Templated Dye Aggregate System. *Journal of Physical Chemistry A* 2017, 121 (37), 6905-6916.
12. Fothergill, J. W.; Hernandez, A. C.; Knowlton, W. B.; Yurke, B.; Li, L., Ab Initio Studies of Exciton Interactions of Cy5 Dyes. *Journal of Physical Chemistry A* 2018, 122(46), 8989-8997.
13. Huff, J. S.; Davis, P. H.; Christy, A.; Kellis, D. L.; Kandadai, N.; Toa, Z. S. D.; Scholes, G. D.; Yurke, B.; Knowlton, W. B.; Pensack, R. D., DNA-Templated Aggregates of Strongly Coupled Cyanine Dyes: Nonradiative Decay Governs Exciton Lifetimes. *Journal of Physical Chemistry Letters* 2019, 10 (10), 2386-2392.
14. Huff, J. S.; Turner, D. B.; Mass, O. A.; Patten, L. K.; Wilson, C. K.; Roy, S. K.; Barclay, M. S.; Yurke, B.; Knowlton, W. B.; Davis, P. H.; Pensack, R. D., Excited-State Lifetimes of DNA-Templated Cyanine Dimer, Trimer, and Tetramer Aggregates: The Role of Exciton Delocalization, Dye Separation, and DNA Heterogeneity. *Journal of Physical Chemistry B*2021, 125 (36), 10240-10259.

15. Cunningham, P. D.; Khachatrian, A.; Buckhout-White, S.; Deschamps, J. R.; Goldman, E. R.; Medintz, I. L.; Melinger, J. S., Resonance energy transfer in DNA duplexes labeled with localized dyes. *Journal of Physical Chemistry B* 2014, 118 (50), 14555-14565.
16. Cunningham, P. D.; Kim, Y. C.; Diaz, S. A.; Buckhout-White, S.; Mathur, D.; Medintz, I. L.; Melinger, J. S., Optical Properties of Vibronically Coupled Cy3 Dimers on DNA Scaffolds. *Journal of Physical Chemistry B* 2018, 122 (19), 5020-5029.
17. Rolczynski, B. S.; Diaz, S. A.; Kim, Y. C.; Medintz, I. L.; Cunningham, P. D.; Melinger, J. S., Understanding Disorder, Vibronic Structure, and Delocalization in Electronically Coupled Dimers on DNA Duplexes. *The Journal of Physical Chemistry A* 2021, 125 (44), 9632-9644.
18. Cannon, B. L.; Patten, L. K.; Kellis, D. L.; Davis, P. H.; Lee, J.; Graugnard, E.; Yurke, B.; Knowlton, W. B., Large Davydov Splitting and Strong Fluorescence Suppression: An Investigation of Exciton Delocalization in DNA-Templated Holliday Junction Dye Aggregates. *Journal of Physical Chemistry A* 2018, 122 (8), 2086-2095.
19. Markova, L. I.; Malinovskii, V. L.; Patsenker, L. D.; Haner, R., J- vs. H-type assembly: pentamethine cyanine (Cy5) as a near-IR chiroptical reporter. *Chemical Communications* 2013, 49 (46), 5298-5300.
20. Mass, O. A.; Wilson, C. K.; Roy, S. K.; Barclay, M. S.; Patten, L. K.; Terpetschnig, E. A.; Lee, J.; Pensack, R. D.; Yurke, B.; Knowlton, W. B., Exciton Delocalization in Indolenine Squaraine Aggregates Templated by DNA Holliday Junction Scaffolds. *Journal of Physical Chemistry B* 2020, 124 (43), 9636-9647.
21. Kostov, O.; Liboska, R.; Pay, O.; Novak, P.; Rosenberg, I., Solid-Phase Synthesis of Phosphorothioate/Phosphonothioate and Phosphoramidate/Phosphonamidate Oligonucleotides. *Molecules* 2019, 24 (10).
22. Kosuri, S.; Church, G. M., Large-scale de novo DNA synthesis: technologies and applications. *Nature Methods* 2014, 11 (5), 499-507.
23. Madsen, M.; Gothelf, K. V., Chemistries for DNA Nanotechnology. *Chemical Reviews* 2019, 119 (10), 6384-6458.
24. Biaggne, A.; Knowlton, W. B.; Yurke, B.; Lee, J.; Li, L., Substituent Effects on the Solubility and Electronic Properties of the Cyanine Dye Cy5: Density Functional and Time-Dependent Density Functional Theory Calculations. *Molecules* 2021, 26 (3).
25. Brush, C. K.; Anderson, E. D. Preparation of indocarbocyanine dye-linked phosphoramidites. U.S. Pat. No. 5,556,959, 1996.
26. Brush, C. K.; Anderson, E. D. Preparation of indocarbocyanine and benzindocarbocyanine dye-linked phosphoramidites. U.S. Pat. No. 5,808,044, 1998.
27. Owens, E. A.; Hyun, H.; Dost, T. L.; Lee, J. H.; Park, G.; Pham, D. H.; Park, M. H.; Choi, H. S.; Henary, M., Near-Infrared Illumination of Native Tissues for Image-Guided Surgery. *Journal of Medicinal Chemistry* 2016, 59 (11), 5311-5323.
28. Caram, J. R.; Doria, S.; Eisele, D. M.; Freyria, F. S.; Sinclair, T. S.; Rebentrost, P.; Lloyd, S.; Bawendi, M. G., Room-Temperature Micron-Scale Exciton Migration in a Stabilized Emissive Molecular Aggregate. *Nano Letters* 2016, 16 (11), 6808-6815.
29. Cao, W.; Sletten, E. M., Fluorescent Cyanine Dye J-Aggregates in the Fluorous Phase. *Journal of the American Chemical Society* 2018, 140 (8), 2727-2730.
30. Mishra, A.; Behera, R. K.; Behera, P. K.; Mishra, B. K.; Behera, G. B., Cyanines during the 1990s: A Review. *Chem. Rev.* (*Washington, D.C.*) 2000, 100 (6), 1973-2011.
31. Izuta, S.; Yamaguchi, S.; Kosaka, T.; Okamoto, A., Reversible and Photoresponsive Immobilization of Nonadherent Cells by Spiropyran-Conjugated PEG-Lipids. *ACS Applied Bio Materials* 2019, 2 (1), 33-38.
32. Kim, S. H.; Hwang, S. H., Synthesis and photostability of functional squarylium dyes. *Dyes Pigm.* 1997, 35 (2), 111-121.
33. Hemmer, J. R.; Smith, P. D.; Horn, M.; Alnemrat, S.; Mason, B. P.; Alaniz, J. R.; Osswald, S.; Hooper, J. P., High strain-rate response of spiropyran mechanophores in PMMA. *J. Polym. Sci., Part B: Polym. Phys.* 2014, 52 (20), 1347-1356.
34. Liu, Q.; Kanahashi, K.; Matsuki, K.; Manzhos, S.; Feron, K.; Bottle, S. E.; Tanaka, K.; Nanseki, T.; Takenobu, T.; Tanaka, H.; Sonar, P., Triethylene Glycol Substituted Diketopyrrolopyrrole- and Isoindigo-Dye Based Donor-Acceptor Copolymers for Organic Light-Emitting Electrochemical Cells and Transistors. *Adv. Electron. Mater.* 2020, 6 (5), 1901414.
35. Baba, A.; Shibata, I.; Fujiwara, M.; Matsuda, H., Novel use of organotin halide-base complex in organic synthesis. Cycloaddition reaction of oxetane with isocyanates. *Tetrahedron Lett.* 1985, 26 (42), 5167.
36. Owens, E. A.; Hyun, H.; Tawney, J. G.; Choi, H. S.; Henary, M., Correlating Molecular Character of NIR Imaging Agents with Tissue-Specific Uptake. *Journal of Medicinal Chemistry* 2015, 58 (10), 4348-4356.
37. Michie, M. S.; Götz, R.; Franke, C.; Bowler, M.; Kumari, N.; Magidson, V.; Levitus, M.; Loncarek, J.; Sauer, M.; Schnermann, M. J., Cyanine Conformational Restraint in the Far-Red Range. *Journal of the American Chemical Society* 2017, 139 (36), 12406-12409.
38. Smith, M.; Rammler, D. H.; Goldberg, I. H.; Khorana, H. G., Studies on Polynucleotides. XIV.1 Specific Synthesis of the C3"-C5" Interribonucleotide Linkage. Syntheses of Uridylyl-(3"→5")-Uridine and Uridylyl-(3"→5")-Adenosine2. *Journal of the American Chemical Society* 1962, 84 (3), 430-440.
39. Fukui, K.; Morimoto, M.; Segawa, H.; Tanaka, K.; Shimidzu, T., Synthesis and properties of an oligonucleotide modified with an acridine derivative at the artificial abasic site. *Bioconjugate Chemistry* 1996, 7(3), 349-355.
40. Nielsen, J.; Taagaard, M.; Marugg, J. E.; Van Boom, J. H.; Dahl, O., Application of 2-cyanoethyl N,N,N',N'-tetraisopropylphosphorodiamidite for in situ preparation of deoxyribonucleoside phosphoramidites and their use in polymer-supported synthesis of oligodeoxyribonucleotides. *Nucleic Acids Res.* 1986, 14(18), 7391.
41. Klein, M.; Ugi, I., Chloro-N,N-dialkylamino-2,2,2-trichloro-tert-butoxy-phosphines, New Reagents in the Syntheses of Oligonucleotides. *Zeitschrift für Naturforschung B* 1995, 50 (6), 948-952.
42. Williams, D. B. G.; Lawton, M., Drying of Organic Solvents: Quantitative Evaluation of the Efficiency of Several Desiccants. *J. Org. Chem.* 2010, 75 (24), 8351-8354.
43. Biosystems, A., Expedite™ 8900 Nucleic Acid Synthesis System User's Guide. Applied Biosystems: Foster City, CA USA, 2001; Vol. Part Number PB601306 Rev. 2.
44. Leo, A.; Hansch, C.; Elkins, D., Partition coefficients and their uses. *Chemical Reviews* 1971, 71 (6), 525-616.

45. Dearden, J. C.; Bresnen, G. M., The measurement of partition coefficients. *Quant. Struct.-Act. Relat.* 1988, 7(3), 133.
46. Sliwoski, G.; Kothiwale, S.; Meiler, J.; Lowe Edward, W., Computational methods in drug discovery. *Pharmacol. Rev.* 2014, 66 (1), 334.
47. Sentell, K. B.; Dorsey, J. G., Retention mechanisms in reversed-phase liquid chromatography. Stationary-phase bonding density and partitioning. *Analytical Chemistry* 1989, 61 (9), 930-934.
48. Rafferty, J. L.; Zhang, L.; Siepmann, J. I.; Schure, M. R., Retention Mechanism in Reversed-Phase Liquid Chromatography: A Molecular Perspective. *Analytical Chemistry* 2007, 79 (17), 6551-6558.
49. Neue, U. D., HPLC Columns, Theory, Technology, and Practice. *Instrumentation Science & Technology* 1998, 26 (4), 439-440.
50. Mandal, A. K.; Taniguchi, M.; Diers, J. R.; Niedzwiedzki, D. M.; Kirmaier, C.; Lindsey, J. S.; Bocian, D. E; Holten, D., Photophysical Properties and Electronic Structure of Porphyrins Bearing Zero to Four meso-Phenyl Substituents: New Insights into Seemingly Well Understood Tetrapyrroles. *The Journal of Physical Chemistry A* 2016, 120 (49), 9719-9731.
51. Breslauer, K. J.; Frank, R.; Bloecker, H.; Marky, L. A., Predicting DNA duplex stability from the base sequence. *Proc. Natl. Acad. Sci. U.S.A* 1986, 83 (11), 3746.
52. Sugimoto, N.; Nakano, S.-i.; Yoneyama, M.; Honda, K.-i., Improved thermodynamic parameters and helix initiation factor to predict stability of DNA duplexes. *Nucleic Acids Res.* 1996, 24 (22), 4501-4505.
53. SantaLucia, J.; Allawi, H. T.; Seneviratne, P. A., Improved Nearest-Neighbor Parameters for Predicting DNA Duplex Stability. *Biochemistry* 1996, 35 (11), 3555-3562.
54. Turro, N. J.; Ramamurthy, V.; Scaiano, J. C., *Modern Molecular Photochemistry of Organic Molecules*. University Science Books: Melville, NY USA, 2010.
55. Patra, D.; Malaeb, N. N.; Haddadin, M. J.; Kurth, M. J., Influence of Substituent and Solvent on the Radiative Process of Singlet Excited States of Novel Cyclic Azacyanine Derivatives. *Journal of Fluorescence* 2012, 22 (2), 707-717.
56. Lewis, J. E.; Maroncelli, M., On the (uninteresting) dependence of the absorption and emission transition moments of coumarin 153 on solvent. *Chemical Physics Letters* 1998, 282 (2), 197-203.
57. Fulmer, G. R.; Miller, A. J. M.; Sherden, N. H.; Gottlieb, H. E.; Nudelman, A.; Stoltz, B. M.; Bercaw, J. E.; Goldberg, K. I., NMR Chemical Shifts of Trace Impurities: Common Laboratory Solvents, Organics, and Gases in Deuterated Solvents Relevant to the Organometallic Chemist. *Organometallics* 2010, 29 (9), 2176-2179.
58. Breger, J. C.; Susumu, K.; Lasarte-Aragones, G.; Diaz, S. A.; Brask, J.; Medintz, I. L., Quantum Dot Lipase Biosensor Utilizing a Custom-Synthesized Peptidyl-Ester Substrate. *Acs Sensors* 2020, 5 (5), 1295-1304.
59. Gemmill, K. B.; Diaz, S. A.; Blanco-Canosa, J. B.; Deschamps, J. R.; Pons, T.; Liu, H. W.; Deniz, A.; Melinger, J.; Oh, E.; Susumu, K.; Stewart, M. H.; Hastman, D. A.; North, S. H.; Delehanty, J. B.; Dawson, P. E.; Medintz, I. L., Examining the Polyproline Nanoscopic Ruler in the Context of Quantum Dots. *Chemistry of Materials* 2015, 27(18), 6222-6237.
60. Drexhage, K. H., Fluorescence efficiency of laser dyes. *J. Res. Natl. Bur. Stand., Sect. A* 1976, 80A (3), 421.
61. Sens, R.; Drexhage, K. H., Fluorescence quantum yield of oxazine and carbazine laser dyes. *J. Lumin.* 1981, 24-25 (2), 709.
62. Boeneman, K.; Prasuhn, D. E.; Blanco-Canosa, J. B.; Dawson, P. E.; Melinger, J. S.; Ancona, M.; Stewart, M. H.; Susumu, K.; Huston, A.; Medintz, I. L., Self-Assembled Quantum Dot-Sensitized Multivalent DNA Photonic Wires. *Journal of the American Chemical Society* 2010, 132 (51), 18177-18190.
63. Algar, W. R.; Khachatrian, A.; Melinger, J. S.; Huston, A. L.; Stewart, M. H.; Susumu, K.; Blanco-Canosa, J. B.; Oh, E.; Dawson, P. E.; Medintz, I. L., Concurrent Modulation of Quantum Dot Photoluminescence Using a Combination of Charge Transfer and Forster Resonance Energy Transfer: Competitive Quenching and Multiplexed Biosensing Modality. *Journal of the American Chemical Society* 2017, 139(1), 363-372.
64. Brown, C. W.; Buckhout-White, S.; Diaz, S. A.; Melinger, J. S.; Ancona, M. G.; Goldman, E. R.; Medintz, I. L., Evaluating Dye-Labeled DNA Dendrimers for Potential Applications in Molecular Biosensing. *ACS Sensors* 2017, 2 (3), 401-410.

What is claimed is:

1. A Cy5 derivative comprising a compound having the structure:

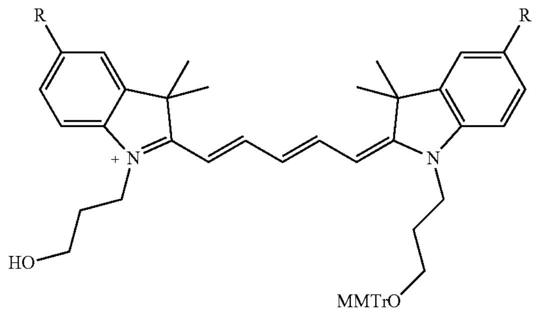

wherein MMTr is 4-monomethoxytrityl and R is selected from the group consisting of —$O(CH_2)_5CH_3$, —$O(CH_2CH_2O)_3CH_3$), —$C(CH_3)_3$, and —Cl, and wherein the Cy5 derivative includes a suitable counterion for the compound.

2. A Cy5 derivative according to claim 1, wherein said counterion is iodide.

3. A nucleic acid in a state of having been synthesized to incorporate a Cy5 derivative according to claim 1.

4. The Cy5 derivative of claim 1, wherein R is —$O(CH_2)_5CH_3$.

5. The Cy5 derivative of claim 1, wherein R is —$O(CH_2CH_2O)_3CH_3$).

6. The Cy5 derivative of claim 1, wherein R is —$C(CH_3)_3$.

7. The Cy5 derivative of claim 1, wherein R is —Cl.

8. A Cy5 derivative comprising a compound having the structure:

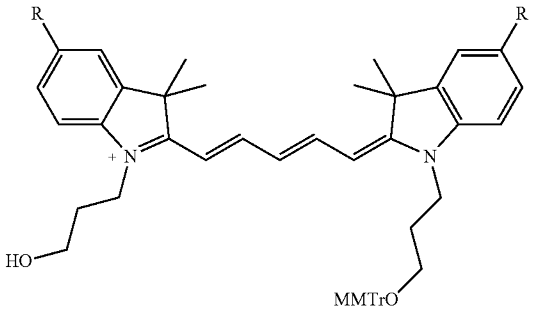

wherein MMTr is 4-monomethoxytrityl and R is selected from the group consisting of consisting of —$CF_3$ and —CN, and wherein the Cy5 derivative includes a suitable counterion for the compound.

9. The Cy5 derivative of claim 8, wherein said counterion is iodide.

10. A method of synthesizing a Cy5 derivative according to claim 1, comprising, in order:

preparing an N-alkyl indolinium iodide salt precursor;

coupling the iodide salt precursor with malonaldehyde dianilide hydrocholoride; and conducting a substitution reaction with 4-monomethoxytrityl chloride (MMTr-Cl).

11. The method of claim 10, wherein said Cy 5 derivative is purified by iterative powderization.

12. The method of claim 10, wherein R is —$O(CH_2)_5CH_3$.

13. The method of claim 10, wherein R is —$O(CH_2CH_2O)_3CH_3$).

14. The method of claim 10, wherein R is —$C(CH_3)_3$.

15. The method of claim 10, wherein R —Cl.

* * * * *

SEQUENCE LISTING

```
Sequence total quantity: 5
SEQ ID NO: 1            moltype = DNA  length = 26
FEATURE                 Location/Qualifiers
source                  1..26
                        mol_type = other DNA
                        organism = synthetic construct
misc_feature            13..14
                        note = site of Cy5 analog incorporation
SEQUENCE: 1
atataatcgc tcgcatatta tgactg                                        26

SEQ ID NO: 2            moltype = DNA  length = 26
FEATURE                 Location/Qualifiers
source                  1..26
                        mol_type = other DNA
                        organism = synthetic construct
misc_feature            13..14
                        note = site of Cy5 analog incorporation
SEQUENCE: 2
cagtcataat atgtggaatg tgagtg                                        26

SEQ ID NO: 3            moltype = DNA  length = 26
```

-continued

```
FEATURE                Location/Qualifiers
source                 1..26
                       mol_type = other DNA
                       organism = synthetic construct
misc_structure         13..14
                       note = site of Cy5 analog incorporation
SEQUENCE: 3
cactcacatt ccactcaaca ccacaa                                       26

SEQ ID NO: 4           moltype = DNA  length = 26
FEATURE                Location/Qualifiers
source                 1..26
                       mol_type = other DNA
                       organism = synthetic construct
misc_feature           13..14
                       note = site of Cy5 analog incorporation
SEQUENCE: 4
ttgtggtgtt gagcgagcga ttatat                                       26

SEQ ID NO: 5           moltype = DNA  length = 26
FEATURE                Location/Qualifiers
source                 1..26
                       mol_type = other DNA
                       organism = synthetic construct
misc_feature           13..14
                       note = site of Cy5 analog incorporation
SEQUENCE: 5
cagtcataat atgcgagcga ttatat                                       26
```